US012366571B2

(12) United States Patent
Li et al.

(10) Patent No.: US 12,366,571 B2
(45) Date of Patent: Jul. 22, 2025

(54) LUMINESCENT OXYGEN CHANNELING IMMUNOASSAY UTILIZING THREE ANTIBODIES AND METHODS OF PRODUCTION AND USE THEREOF

(71) Applicant: Siemens Healthcare Diagnostics Inc., Tarrytown, NY (US)

(72) Inventors: Jay J. Li, Franklin, MA (US); David J. Ledden, Elkhart, IN (US); Eric Scott Cowden, Waltham, MA (US); Donglai Lu, Chandler, AZ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 664 days.

(21) Appl. No.: 17/155,642

(22) Filed: Jan. 22, 2021

(65) Prior Publication Data

US 2021/0231647 A1 Jul. 29, 2021

Related U.S. Application Data

(62) Division of application No. 15/128,479, filed as application No. PCT/US2015/022209 on Mar. 24, 2015, now abandoned.

(60) Provisional application No. 61/970,596, filed on Mar. 26, 2014.

(51) Int. Cl.
| | |
|---|---|
| *G01N 33/53* | (2006.01) |
| *G01N 21/76* | (2006.01) |
| *G01N 33/542* | (2006.01) |
| *G01N 33/543* | (2006.01) |
| *G01N 33/58* | (2006.01) |

(52) U.S. Cl.
CPC ......... *G01N 33/5308* (2013.01); *G01N 21/76* (2013.01); *G01N 33/542* (2013.01); *G01N 33/54306* (2013.01); *G01N 33/54366* (2013.01); *G01N 33/582* (2013.01); *G01N 2800/32* (2013.01); *G01N 2800/325* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,340,716 A | 8/1994 | Ullman et al. | |
| 5,585,241 A | 12/1996 | Lindmo | |
| 6,251,581 B1 * | 6/2001 | Ullman | C07D 265/30 252/700 |
| 6,703,248 B1 * | 3/2004 | Singh | G01N 33/587 436/523 |
| 8,414,896 B2 * | 4/2013 | Pedersen | C07K 16/2863 424/174.1 |
| 9,678,068 B2 | 6/2017 | Duffy | |
| 2003/0040024 A1 * | 2/2003 | Katrukha | G01N 33/6887 435/7.93 |
| 2005/0170443 A1 | 8/2005 | Cantor | |
| 2006/0263907 A1 * | 11/2006 | Zweig | G01N 33/5306 436/524 |
| 2007/0183934 A1 * | 8/2007 | Diercks | G01N 15/1484 422/400 |
| 2009/0087859 A1 | 4/2009 | Johnson | |
| 2009/0170218 A1 | 7/2009 | Zheng et al. | |
| 2011/0053289 A1 | 3/2011 | Lowe et al. | |
| 2012/0045847 A1 | 2/2012 | Lewisch et al. | |
| 2012/0288961 A1 | 11/2012 | Yager et al. | |
| 2016/0320415 A1 | 11/2016 | Manneh | |

FOREIGN PATENT DOCUMENTS

| | | | | |
|---|---|---|---|---|
| CN | 102565381 A | | 7/2012 | |
| EP | 0984282 A2 * | | 5/1992 | G01N 33/58 |
| EP | 1521843 B1 | | 9/2007 | |
| JP | 2002214237 A | | 7/2002 | |
| JP | 2005510706 A | | 4/2005 | |
| JP | 2011512318 A | | 4/2011 | |
| JP | 2013068627 A | | 4/2013 | |
| WO | 9202551 A1 | | 2/1992 | |
| WO | WO 9517675 | * | 6/1995 | G01N 33/543 |
| WO | 9946597 A1 | | 9/1999 | |
| WO | 2013078130 A1 | | 5/2013 | |
| WO | 2014151450 A1 | | 9/2014 | |
| WO | 2014151590 A1 | | 9/2014 | |
| WO | 2014152165 A1 | | 9/2014 | |
| WO | 2014152322 A1 | | 9/2014 | |
| WO | WO 2015013671 | * | 1/2015 | C07K 16/28 |

OTHER PUBLICATIONS

International Search Report and Written Opinion of International Application No. PCT/US2015/022209 dated Jul. 8, 2015.
Kohler et al., "Continuous cultures of fused cells secreting antibody of predefined specificity"; Aug. 7, 1975; Nature 256, pp. 495-497.
Aubry, "Search for singlet oxygen in the decomposition of hydrogen peroxide by mineral compounds in aqueous solutions"; 1985, J. Am. Chem. Soc., 107 (21), pp. 5844-5849.
Aubry et al., "Chemical sources of singlet oxygen. 3. Peroxidalion of water-soluble singlet oxygen carriers with the hydrogen peroxide-molybdate system"; 1989, J. Org. Chem., 54 (3), pp. 726-728.
Chothia et al., "Conformations of immunoglobulin hypervariable regions"; Dec. 28, 1989; Nature 342, pp. 877-883.
Clackson et al., "Making antibody fragments using phage display libraries"; Aug. 15, 1991; Nature 352, pp. 524-628.
Marks et al., "By-passing immunization. Human antibodies from V-gene libraries displayed on phage"; 1991; J Mol Biol. 222(3): pp. 581-597.
Böhme et al., "Generation of singlet oxygen from hydrogen peroxide disproportionation catalyzed by molybdate ions"; 1992; Inorg. Chem., 31 (16), pp. 3468-3471.
Niu et al., "Singlet molecular oxygen generation from the decomposition of sodium peroxotungstate and sodium peroxomolybdate"; 1992; Inorg. Chem., 31 (16), pp. 3472-3476.

(Continued)

*Primary Examiner* — Ann Montgomery

(57) ABSTRACT

A chemiluminescent detection system, as well as kits and microfluidics devices containing same, are disclosed. Methods of using the system, kits, and devices are also disclosed.

20 Claims, 11 Drawing Sheets

Specification includes a Sequence Listing.

(56) References Cited

OTHER PUBLICATIONS

Nardello et al., "90Mo NMR and kinetic studies of peroxomolybdic intermediates involved in the catalytic disproportionation of hydrogen peroxide by molybdate ions"; 1995; Inorg. Chem., 34 (20), pp. 4950-4957.

Babcock et al., "A novel strategy for generating monoclonal antibodies from single, isolated lymphocytes producing antibodies of defined specificities"; Jul. 1996; Proc. Natl. Acad. Sci. USA; Immunology vol. 93(15): pp. 7843-7848.

Aubry et al., "Preparative Oxidation of Organic Compounds in Microemulsions with Singlet Oxygen Generated Chemically by the Sodium Molybdate/Hydrogen Peroxide System1"; 1997, J. Am. Chem. Soc., 119 (23), pp. 5286-5294.

Alpert et al., "Myocardial infarction redefined—a consensus document of The Joint European Society of Cardiology/American College of Cardiology Committee for the redefinition of myocardial infarction"; Sep. 2000.; J. Am. Coll. Cardiol.; vol. 36(3): pp. 959-969.

Almeida et al., "Direct evidence of singlet molecular oxygen [O 2 (1Δ g ) ] production in the reaction of acetonitrile with hydrogen peroxide in alkaline solutions"; Apr. 2003; Analytica Chimica Acta 482(1): pp. 99-104.

Hudson et al., "Engineered antibodies"; Jan. 2003; Nature Medicine 9 (1), pp. 129-134.

European Search Report and Written Opinion of European Application No. 15767906.9 dated Feb. 20, 2017.

European Search Report and Written Opinion of European Application No. 18199087.0 dated Jan. 28, 2019.

Perkinelmer, Alpha Technologies for Antibody Detection and Characterization, Alpha Technology: Biotherapeutics Applications, 2011, pp. 1-6.

\* cited by examiner

| | | 10 | 20 | 30 | 40 | 50 |
|---|---|---|---|---|---|---|
| cTnI_hum | N-TERM | M A D G S S D A A R | E P R P A P A P I R | R R S*S*N Y R A Y A T E P H A K K K S K | | I S A S R K L Q L K |
| | | | | DETECTION mAb-1 / DETECTION mAb-2 | | CAPTURE mAb |

| | 60 | 70 | 80 | 90 | 100 |
|---|---|---|---|---|---|
| cTnI_hum | T L L L Q I A K Q E | L E R E A E E R R G | E K G R A L S T R C | Q P L E L A G L G F | A E L Q D L C R Q L |
| | CAPTURE mAb | | | | |

| | 110 | 120 | 130 | 140 | 150 |
|---|---|---|---|---|---|
| cTnI_hum | H A R I V D K V D E E | R Y D I E A K V T K | N I T E I A D L T Q | K I F D L R G K F K | R P T L R R V R I S |

| | 160 | 170 | 180 | 190 | 200 |
|---|---|---|---|---|---|
| cTnI_hum | A D A M M Q A L L G | A R A K E S L D L R | A H L K Q V K K E D | T E K E N R E V G D | W R K N I D A L S G |
| | | | 185* | | |

| | 210 | | | | |
|---|---|---|---|---|---|
| cTnI_hum | M E G R K K K F E S | C-TERM | | | |

| cTnI_hum | N-TERM M A D G S S D A A R | 10 E | P R P A P I A P I R | 20 R | R I S* S* N Y R A Y A T E P H A K K K S | 30 CAPTURE Ab 1 (Ab POOL) DETECTOR Ab 2 (mAb) | 40 K | T S A S R K L Q L | 50 K CAPTURE Ab (mAb) |

| cTnI_hum | T I L L Q I A K Q E CAPTURE Ab (mAb) | 60 L | E R E A E E R R G | 70 E | K G R A L S T R C Q P L E L L A G L G F | 80 | A | E I L Q D L C R Q L | 100 L |

| cTnI_hum | H A R V D K V D E E | 110 R | Y D L E A K V T K | 120 N | I T E I A D L T Q K I F D L R G K F K | 130 | R | P T I L R R V R I | 150 S |

| cTnI_hum | A D A M M Q A L L G | 160 A | R A K E S L D L R | 170 A | H L K Q V L K E D T E K E N R E V G I D | 180 185* | W | R K N I D A L S | 200 G |

| cTnI_hum | M E G R K K K F E S | 210 C-TERM |

| cInl_hum | N-TERM | | | | | | | | | | 10 | | | | | | | | | | 20 | | | | | | | | | | 30 | | | | | | | | | | 40 | | | | | | | | | | 50 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | M | A | D | G | S | S | D | I | A | A | R | E | P | R | P | A | P | I | A | P | L | R | R | R | S | * | S | N | V | R | A | Y | A | T | E | P | H | A | K | K | K | S | K | T | S | A | S | R | K | L | Q | L | K |
| | | | | | | | | | | | | | | | | | | | | CAPTURE Ab (mAb) | | | | | | | | | | | | | DETECTOR Ab (Yag P006) | | | | | | | | | | | | | | | | | | |

| cInl_hum | | | | | | | | | | 60 | | | | | | | | | | 70 | | | | | | | | | | 80 | | | | | | | | | | 90 | | | | | | | | | | 100 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | T | L | L | L | Q | I | A | K | Q | E | L | E | I | R | E | A | E | I | R | R | G | E | K | G | R | I | A | L | S | T | R | C | Q | P | L | E | L | A | G | L | G | F | A | E | I | L | Q | D | L | C | R | Q | L |

| cInl_hum | | | | | | | | | | 110 | | | | | | | | | | 120 | | | | | | | | | | 130 | | | | | | | | | | 140 | | | | | | | | | | 150 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | H | A | R | V | D | K | I | V | D | E | R | Y | D | I | L | E | A | K | V | T | K | N | I | T | E | I | A | D | L | T | Q | K | L | F | D | L | R | G | K | F | K | R | P | T | L | R | R | V | R | I | S |

| cInl_hum | | | | | | | | | | 160 | | | | | | | | | | 170 | | | | | | | | | | 180 | | | | | 185* | | | | | 190 | | | | | | | | | | 200 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | A | D | A | M | M | Q | A | L | L | G | A | I | R | A | K | E | S | I | A | D | L | R | A | H | L | K | Q | V | K | E | D | T | E | K | E | N | R | E | I | V | G | D | W | R | I | K | N | I | D | A | L | S | G |
| | | | | | | | | | | | | | | | | | | | | | | | | | | | | | | | | | | | | | | | | | | | CAPTURE Ab 2 (mAb) | | | | | | | | |

| cInl_hum | 210 | | C-TERM | | |
|---|---|---|---|---|---|
| | M | E | G | R | K | K | K | F | E | L | S |

SEQUENCE LISTING

```
<160> NUMBER OF SEQ ID NOS: 18

<210> SEQ ID NO 1
<211> LENGTH: 210
<212> TYPE: PRT
<213> ORGANISM: Homo sapiens

<400> SEQUENCE: 1

Met Ala Asp Gly Ser Ser Asp Ala Ala Arg Glu Pro Arg Pro Ala Pro
1               5                   10                  15

Ala Pro Ile Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
            35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser
    210

<210> SEQ ID NO 2
<211> LENGTH: 18
<212> TYPE: PRT
<213> ORGANISM: Homo sapiens
```

-continued

```
<400> SEQUENCE: 2

Glu Pro Arg Pro Ala Pro Ala Pro Ile Arg Arg Arg Ser Ser Asn Tyr
1               5                   10                  15

Arg Ala

<210> SEQ ID NO 3
<211> LENGTH: 14
<212> TYPE: PRT
<213> ORGANISM: Homo sapiens

<400> SEQUENCE: 3

Tyr Arg Ala Tyr Ala Thr Glu Pro His Ala Lys Lys Lys Ser
1               5                   10

<210> SEQ ID NO 4
<211> LENGTH: 16
<212> TYPE: PRT
<213> ORGANISM: Homo sapiens

<400> SEQUENCE: 4

Lys Ile Ser Ala Ser Arg Lys Leu Gln Leu Lys Thr Leu Leu Leu Gln
1               5                   10                  15

<210> SEQ ID NO 5
<211> LENGTH: 13
<212> TYPE: PRT
<213> ORGANISM: Homo sapiens

<400> SEQUENCE: 5

Leu Glu Leu Ala Gly Leu Gly Phe Ala Glu Leu Gln Asp
1               5                   10

<210> SEQ ID NO 6
<211> LENGTH: 20
<212> TYPE: PRT
<213> ORGANISM: Homo sapiens

<400> SEQUENCE: 6

Leu Arg Ala His Leu Lys Gln Val Lys Lys Glu Asp Thr Glu Lys Glu
1               5                   10                  15

Asn Arg Glu Val
            20

<210> SEQ ID NO 7
<211> LENGTH: 8
<212> TYPE: PRT
<213> ORGANISM: Homo sapiens

<400> SEQUENCE: 7

Gly Asp Trp Arg Lys Asn Ile Asp
1               5

<210> SEQ ID NO 8
<211> LENGTH: 7
<212> TYPE: PRT
<213> ORGANISM: Homo sapiens

<400> SEQUENCE: 8

Tyr Arg Ala Tyr Ala Thr Glu
1               5

<210> SEQ ID NO 9
<211> LENGTH: 5
```

```
<212> TYPE: PRT
<213> ORGANISM: Homo sapiens

<400> SEQUENCE: 9

Ala Thr Glu Pro His
1               5

<210> SEQ ID NO 10
<211> LENGTH: 15
<212> TYPE: PRT
<213> ORGANISM: Homo sapiens

<400> SEQUENCE: 10

Ile Ser Ala Ser Arg Lys Leu Gln Leu Lys Thr Leu Leu Leu Gln
1               5                   10                  15

<210> SEQ ID NO 11
<211> LENGTH: 12
<212> TYPE: PRT
<213> ORGANISM: Homo sapiens

<400> SEQUENCE: 11

Ala Tyr Ala Thr Glu Pro His Ala Lys Lys Lys Ser
1               5                   10

<210> SEQ ID NO 12
<211> LENGTH: 13
<212> TYPE: PRT
<213> ORGANISM: Homo sapiens

<400> SEQUENCE: 12

Arg Ala Tyr Ala Thr Glu Pro His Ala Lys Lys Lys Ser
1               5                   10

<210> SEQ ID NO 13
<211> LENGTH: 9
<212> TYPE: PRT
<213> ORGANISM: Homo sapiens

<400> SEQUENCE: 13

Val Gly Asp Trp Arg Lys Asn Ile Asp
1               5

<210> SEQ ID NO 14
<211> LENGTH: 16
<212> TYPE: PRT
<213> ORGANISM: Homo sapiens

<400> SEQUENCE: 14

Glu Pro Arg Pro Ala Pro Ala Pro Ile Arg Arg Arg Ser Ser Asn Tyr
1               5                   10                  15

<210> SEQ ID NO 15
<211> LENGTH: 32
<212> TYPE: PRT
<213> ORGANISM: Homo sapiens

<400> SEQUENCE: 15

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
                20                  25                  30

<210> SEQ ID NO 16
```

```
<211> LENGTH: 6
<212> TYPE: PRT
<213> ORGANISM: Homo sapiens

<400> SEQUENCE: 16

Lys Val Leu Arg Arg His
1               5

<210> SEQ ID NO 17
<211> LENGTH: 7
<212> TYPE: PRT
<213> ORGANISM: Homo sapiens

<400> SEQUENCE: 17

Cys Lys Val Leu Arg Arg His
1               5

<210> SEQ ID NO 18
<211> LENGTH: 9
<212> TYPE: PRT
<213> ORGANISM: Homo sapiens

<400> SEQUENCE: 18

Val Gln Gly Ser Gly Cys Phe Gly Arg
1               5
```

LUMINESCENT OXYGEN CHANNELING IMMUNOASSAY UTILIZING THREE ANTIBODIES AND METHODS OF PRODUCTION AND USE THEREOF

CROSS REFERENCE TO RELATED APPLICATIONS/INCORPORATION BY REFERENCE STATEMENT

This application is a divisional of U.S. Ser. No. 15/128,479, filed Sep. 23, 2016; which is a US national stage application filed under 35 USC § 371 of International Application No. PCT/US2015/022209, filed Mar. 24, 2015; which claims benefit under 35 USC § 119(e) of U.S. Ser. No. 61/970,596, filed Mar. 26, 2014. The entire contents of the above-referenced patent application applications are hereby expressly incorporated herein by reference.

This application incorporates by reference the sequence listing which is submitted together with this application in computer readable form which has the file name 2014P07114US01-Seq_Listing_ST25.txt and is 6 KB.

STATEMENT REGARDING FEDERALLY FUNDED RESEARCH OR DEVELOPMENT

Not Applicable.

BACKGROUND

Immunoassay technologies are widely used in the field of medical diagnostics. One example of a commercially used immunoassay is an induced luminescence immunoassay, such as but not limited to, the LOCI® Luminescent Oxygen Channeling Immunoassay technology (Siemens Healthcare Diagnostics Inc., Tarrytown, NY). The induced luminescence immunoassay is described in U.S. Pat. No. 5,340,716 (issued to Ullman et al. on Aug. 23, 1994). The currently available LOCI® technology involves an immunoassay that uses several reagents and requires that two of these reagents (referred to as a "sensibead" and a "chemibead") be brought into close proximity to one another to achieve a signal. Upon exposure to light at a certain wavelength (such as, but not limited to, 680 nm), the sensibead releases singlet oxygen, and if the two beads are in close proximity, the singlet oxygen is transferred to the chemibead; this causes a chemical reaction that results in the chemibead giving off light that can be measured at a different wavelength (such as, but not limited to, 612 nm).

However, there are obstacles that exist for this technology. In particular, the immunoassay is dependent upon the sensitivity and dynamic range of the one or more antibodies that is used as the analyte detection mechanism. For example, certain commercially available antibodies that are currently used in immunoassays (including immunoassays used in a central laboratory and/or point-of care environment) have limited sensitivity. In addition, when the induced luminescence immunoassay technology is applied with an antibody of limited sensitivity in development of a point-of-care (POC) assay that utilizes a microfluidic chip, the sensitivity of the assay is further compromised by the assay format, which utilizes a lower sample volume. Thus, the POC assay may not meet a required assay sensitivity target.

The sensitivity of an analyte detection immunoassay is dependent on the affinity of one or more anti-analyte antibodies employed in the assay architecture: the higher the affinity of the antibody, the higher the sensitivity of the immunoassay. Thus, anti-analyte antibodies having high sensitivity are desired for use in the development of analyte-specific induced luminescence immunoassays. Unfortunately, an antibody that exhibits substantially improved sensitivity over an existing antibody also typically exhibits a much narrower dynamic assay range when compared to the existing antibody.

In a particular, non-limiting Example, one specific analyte for which detection by an induced luminescence immunoassay (such as, but not limited to, a POC induced luminescence immunoassay) is desired is cardiac Troponin I (cTnI). Cardiac troponins are considered the most sensitive and specific biochemical markers for the detection of myocardial damage. The redefinition of an acute myocardial infarction (AMI) by the European Society of Cardiology and American College of Cardiology (ESC/ACC) recommends that an increased level of cardiac troponin should be defined as a measurement above the 99th percentile value of the reference group (Alpert, *J. Am. Coll. Cardiol.*, 36:959-69 (2000)). Moreover, the ESC/ACC recommendation requires that the total imprecision at 99th percentile decision limit be 10% or less (Table 1).

TABLE 1

| Performance Requirements for a cTnI Immunoassay | |
|---|---|
| Minimum Detectable Concentration | 0.006 ng/ml |
| 99th Percentile | 0.04 ng/ml |
| 10% Total CV | 0.03 ng/ml |

These new standards of performance for cardiac troponin assays require new approaches to immunoassay design in order to achieve quantitative and precise measurement of extremely low levels of troponin found in minor or early myocardial damage. Various immunoassay architectures, antibodies, and detection technologies have been suggested to achieve and surpass these new performance standards.

Antibody selection is central to meeting the new performance goals described above. Selection criteria must take into account not only the specificity of cardiac troponin I binding, but also binding affinities, which determine detection limits and assay time. Cross-reactivities to other cardiac and skeletal troponins, as well as other cardiovascular biomarkers, must be insignificant.

In addition, it is critical to measure the total amount of cardiac specific troponin I in a patient sample for maximum analytical sensitivity. Since cardiac troponin I (cTnI) exists as free and as complexed forms with cardiac troponin C (cTnC) and, to a lesser extent, with cardiac Troponin T (cTnT), it is important to select antibodies that bind cTnI epitopes which are expressed independently of complexation with other cardiac troponins. The ability to bind free and complexed forms of cTnI is also important in situations where EDTA plasma is the sample type used. The association constant between cTnI and cTnC is stronger in the presence of $Ca^{2+}$. EDTA chelates $Ca^{2+}$, resulting in an increase in the proportion of free cTnI in the sample. Additionally, the proportion of free and complexed cTnI is modulated to some extent by the degree of cTnI and cTnC proteolysis.

Careful antibody selection is essential to ensure recovery of cTnI after proteolysis both by proteases present in necrotic myocardium and in the patient's plasma. The extent of degradation varies between individual patients. The manifestation of cTnI proteolysis leads to the apparent differences in sample stability between commercially available cTnI methods and stability differences between samples.

Sample stability for cTnI depends on the specific epitopes recognized by the antibodies in the cTnI test system.

Early generations of commercially available anti-cTnI antibodies used in cTnI induced luminescence immunoassays had adequate sensitivity at the time of their introduction; however, once the definition of AMI changed in 2000 (as described herein above), the commercially available anti-cTnI antibodies now exhibited a limited sensitivity at the increased performance requirement levels for cTnI assays. Thus, these antibodies of limited sensitivity did not provide the required assay sensitivity target in the induced luminescence immunoassay format (including both central laboratory and/or point-of care formats). In addition, antibodies of limited sensitivity are even greater obstacles to the development of a point-of-care (POC) assay format that utilizes a microfluidic chip, as the sensitivity of the assay is further compromised by the lower sample volume utilized in the POC assay format.

A newly identified antibody designed for replacement of the current antibody of limited sensitivity (i.e., a high affinity sheep monoclonal anti-cTnI antibody) exhibited substantially improved sensitivity over the existing antibody; however, this new antibody has a much narrower dynamic assay range. Signal plateau was observed at cTnI concentrations above 20 ng/ml, and the enhanced cTnI assay using the new high affinity antibody does not have the required dynamic range of the current commercial cTnI assay.

Thus, new and improved antibody-based induced luminescence immunoassays and assay architectures that exhibit high sensitivity over a large dynamic range are desired. It is to such assays, as well as compositions, kits, devices, and methods related thereto, that the presently disclosed and claimed inventive concept(s) is directed.

DESCRIPTION OF THE SEVERAL VIEWS OF THE DRAWINGS

FIG. 15 contains a cTnI epitope map illustrating a first example of epitopes recognized by a set of three antibodies utilized in a cTnI immunoassay constructed in accordance with the presently disclosed and claimed inventive concept(s).

FIG. 16 contains a cTnI epitope map illustrating a second example of epitopes recognized by a set of three antibodies utilized in a cTnI immunoassay constructed in accordance with the presently disclosed and claimed inventive concept(s). The set of three antibodies recognize three epitopes: two overlapping epitopes recognized by two detection antibodies and a third epitope recognized by a capture antibody, wherein the third epitope does not overlap with the other two epitopes.

FIG. 17 contains a cTnI epitope map illustrating a third example of epitopes recognized by a set of three antibodies utilized in a cTnI immunoassay constructed in accordance with the presently disclosed and claimed inventive concept(s).

FIG. 18 contains a BNP epitope map illustrating a first example of epitopes recognized by a set of three antibodies utilized in a BNP immunoassay constructed in accordance with the presently disclosed and claimed inventive concept(s).

DETAILED DESCRIPTION

Figure 1:
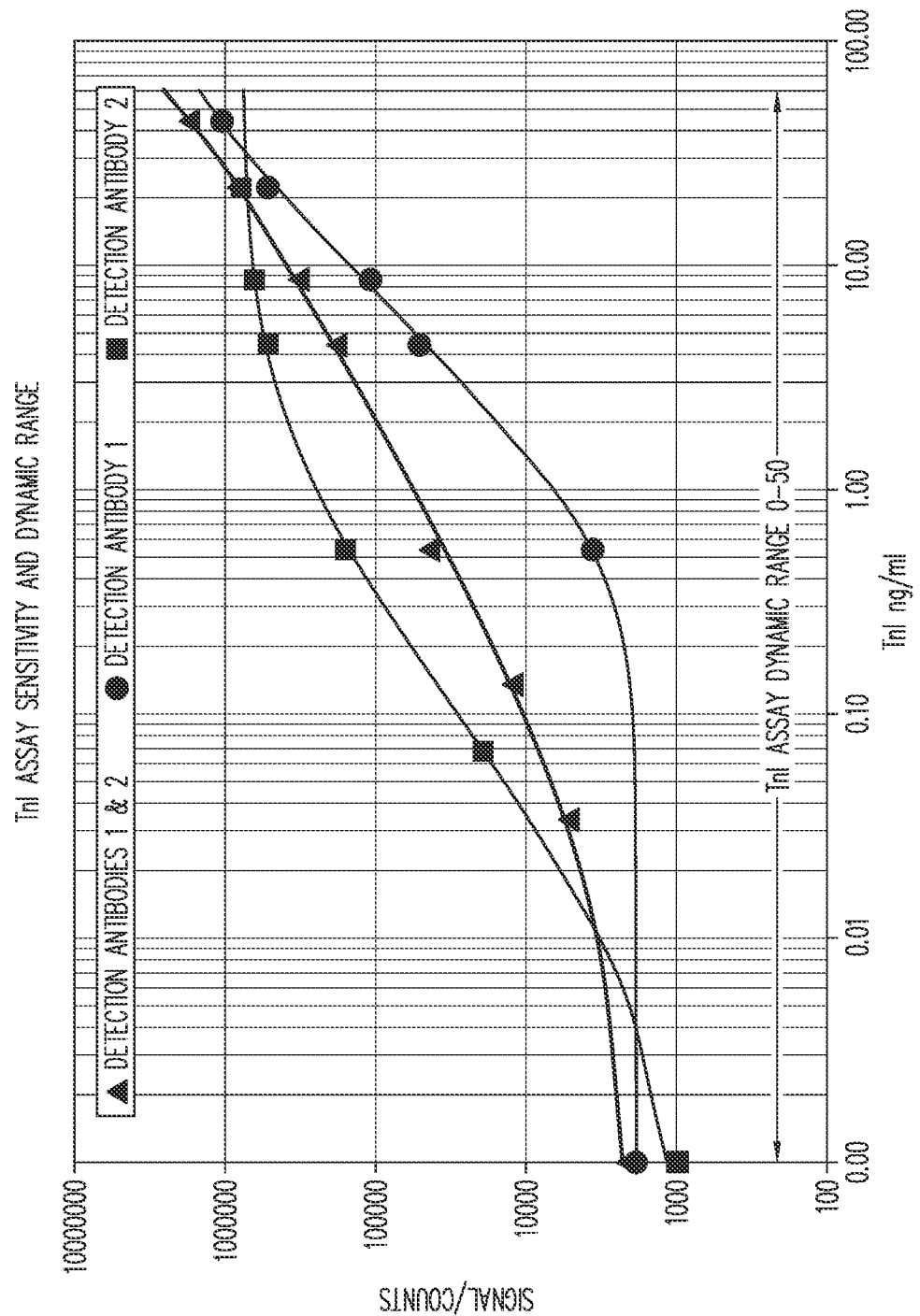
FIG. 1 graphically compares the sensitivity and dynamic range of known prior art cardiac Troponin I (cTnI) immunoassays to the sensitivity and dynamic range of the immunoassays constructed in accordance with the presently disclosed and claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "purified" as used herein means at least one order of magnitude of purification is achieved compared to the starting material or of the natural material, for example but not by way of limitation, two, three, four or five orders of magnitude of purification of the starting material or of the natural material. Thus, the term "purified" as utilized herein does not necessarily mean that the material is 100% purified, and therefore such term does not exclude the presence of other material(s) present in the purified composition.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halogenid selected from fluoride, chloride bromide or iodite, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocycloalkyl, each of which is optionally substituted wherein the optional substitutents are selected from one or more of alkenylalkyl, alkynylalkyl, cycloalkyl, cyclalkenylalkyl, arylalkyl, alkylaryl, heteroarylalkyl, heterocyclealkyl, optionally substituted heterocycloalkenylalkyl, arylcycloalkyl, and arylheterocyclalkyl, phenyl, cyano, hydroxyl, alkyl, aryl, cycloalkyl, cyano, alkoxy, alkylthio, amino, —NH(alkyl), —NH(cycloalkyl)2, carboxy and —C(O))-alkyl.

The term "sample" as used herein will be understood to include any type of biological sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), skin, interstitial fluid, tears, mucus, urine, swabs, combinations, and the like.

The term "binding partner" as used herein will be understood to refer to any molecule capable of associating with another molecule. For example but not byway of limitation, the binding partner may be an antibody (including polyclonal or monoclonal antibodies), antibody fragments (such as but not limited to, Fab, Fab', F(ab')$_2$, Fv, scFv, Fd, diabodies, single-chain antibodies, and other antibody fragments that retain at least a portion of the variable region of an intact antibody), a receptor, a ligand, aptamers, antibody substitute proteins or peptides (i.e., engineered binding proteins/peptides), molecular imprinted polymers (i.e., inorganic matrices), combinations or derivatives thereof, as well as any other molecules capable of specific binding to the analyte.

The term "antibody" is used in the broadest sense, and specifically covers monoclonal antibodies (including full length monoclonal antibodies), polyclonal antibodies, multispecific antibodies (e.g., bispecific antibodies), and antibody fragments so long as they exhibit the desired biological activity. Thus, the terms "Antibody" or "antibody peptide(s)" refer to a full length immunoglobulin molecule (i.e., an intact antibody), or a binding fragment thereof that competes with the intact antibody for specific antigen binding. Binding fragments may be produced by recombinant DNA techniques, or by enzymatic or chemical cleavage of intact antibodies. Binding fragments include Fab, Fab', F(ab')$_2$, Fv, scFv, disulfide linked Fv, Fd, diabodies, single-chain antibodies, single domain antibodies (such as but not limited to, NANOBODIES® (Ablynx, Zwijnaarde, Belgium)), and other antibody fragments that retain at least a portion of the variable region of an intact antibody. See, e.g., Hudson et al. (Nature Med., 9:129-134 (2003)).

The term "antigen binding fragment" or "antigen-binding portion" of an antibody, as used herein, refers to one or more fragments of an antibody that retain the ability to bind to an antigen. The antigen-binding function of an antibody can be performed by fragments of an intact antibody. Examples of binding fragments encompassed within the term "antigen-binding fragment" of an antibody include but are not limited to, Fab, Fab', F(ab')2, Fv, scFv, disulfide linked Fv, Fd, diabodies, single-chain antibodies, single domain antibodies (such as but not limited to, NANOBODIES® (Ablynx, Zwijnaarde, Belgium)), isolated CDRH3, and other antibody fragments that retain at least a portion of the variable region of an intact antibody. These antibody fragments are obtained using conventional recombinant and/or enzymatic techniques and are screened for antigen binding in the same manner as intact antibodies.

The terms "CDR", and its plural "CDRs", refer to a complementarity determining region (CDR) of an antibody or antibody fragment, which determine the binding character of an antibody or antibody fragment. In most instances, three CDRs are present in a light chain variable region (CDRL1, CDRL2 and CDRL3) and three CDRs are present in a heavy chain variable region (CDRH1, CDRH2 and CDRH3). CDRs contribute to the functional activity of an antibody molecule and are separated by amino acid sequences that comprise scaffolding or framework regions. Among the various CDRs, the CDR3 sequences, and particularly CDRH3, are the most diverse and therefore have the strongest contribution to antibody specificity. There are at least two techniques for determining CDRs: (1) an approach based on cross-species sequence variability (i.e., Kabat et al., *Sequences of Proteins of Immunological Interest* (National Institute of Health, Bethesda, Md. (1987)); and (2) an approach based on crystallographic studies of antigen-antibody complexes (Chothia et al., *Nature,* 342:877 (1989)).

The term "epitope" as used herein refers to any protein determinant capable of specific binding to an immunoglobulin or T-cell receptor. In certain embodiments, an epitope is a region of an antigen that is specifically bound by an antibody. Epitopic determinants usually include chemically active surface groupings of molecules, such as but not limited to, amino acids, sugar side chains, phosphoryl, and/or sulfonyl groups. In certain embodiments, an epitope may have specific three dimensional structural characteristics as well as specific charge characteristics.

The term "epitope" as used herein will be understood to include both linear epitopes as well as conformational epitopes. Linear epitopes are formed of a continuous sequence of amino acids from an antigen, and thus comprise an antigen's primary/linear peptide/protein structure. Conformational epitopes are formed of discontinuous sections of an antigen's amino acid sequence and are based upon three dimensional surface features and/or shape of the tertiary structure of an antigen.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

An antibody "specifically binds" an antigen when it preferentially recognizes the antigen in a complex mixture of proteins and/or macromolecules. In certain embodiments, an antibody comprises an antigen-binding site that specifically binds to a particular epitope. In certain such embodiments, the antibody is capable of binding different antigens so long as the different antigens comprise that particular epitope or closely related epitopes. In certain instances, for example, homologous proteins from different species may comprise the same epitope. In certain embodiments, an antibody specifically binds to an antigen with a dissociation constant of no greater than $10^{-6}$ M, $10^{-7}$ M, $10^{-8}$ M, $10^{-9}$ M, $10^{-10}$ M, $10^{-11}$ M, $10^{-12}$ M, or $10^{-13}$ M.

An "isolated" antibody is one which has been separated and/or recovered from a component of the environment in which it was produced. Contaminant components of its production environment are materials which would interfere with diagnostic or therapeutic uses for the antibody, and may include enzymes, hormones, and other proteinaceous or nonproteinaceous solutes. In certain embodiments, the antibody will be purified as measurable by at least three different methods: (1) to greater than 50% by weight of antibody as determined by the Lowry method, such as more than 75% by weight, or more than 85% by weight, or more than 95% by weight, or more than 99% by weight; (2) to a degree sufficient to obtain at least 10 residues of N-terminal or internal amino acid sequence by use of a spinning cup sequenator, such as at least 15 residues of sequence; or (3) to homogeneity by SDS-PAGE under reducing or non-reducing conditions using Coomasie blue or, preferably, silver stain. Isolated antibody includes the antibody in situ within recombinant cells since at least one component of the environment in which the antibody is produced will not be present. Ordinarily, however, isolated antibody will be prepared by at least one purification step. In addition, the "isolated antibody" is substantially free of other antibodies having different antigenic specificities. An isolated antibody may, however, have some cross-reactivity to other, related antigens.

The term "monoclonal antibody" as used herein refers to an antibody obtained from a population of substantially homogeneous antibodies that specifically bind to the same epitope, i.e., the individual antibodies comprising the population are identical except for possible naturally occurring mutations that may be present in minor amounts (although there may be variability in the glycation patterns of the individual antibodies). In contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that in one method of production they may be synthesized by a hybridoma culture, and thus are uncontaminated by other immunoglobulins. The modifier "monoclonal" indicates the character of the antibody as being obtained from a substantially homogeneous population of antibodies, and is not to be construed as requiring production of the antibody by any particular method. For example, in one embodiment, the monoclonal antibodies produced in accordance with the presently disclosed and claimed inventive concept(s) may be made by the hybridoma method first described by Kohler and Milstein (*Nature*, 256:495 (1975)).

Monoclonal antibodies utilized in accordance with the presently disclosed and claimed inventive concept(s) may be produced by any methodology known in the art including, but not limited to, a result of a deliberate immunization protocol; a result of an immune response that results in the production of antibodies naturally in the course of a disease or cancer; phage-derived antibodies; and the like. In addition to the hybridoma production method listed above, the monoclonal antibodies of the presently disclosed and claimed inventive concept(s) may be produced by other various methods such as, but not limited to, recombinant DNA methods (see, e.g., U.S. Pat. No. 4,816,567); isolation of antibody fragments from a phage display library (see, e.g., Clackson et al., *Nature*, 352: 624-628 (1991); and Marks et al., *J. Mol. Biol.*, 222:581-597 (1991)); as well as various other monoclonal antibody production techniques (see, e.g., Harlow and Lane, *Antibodies: A Laboratory Manual* (Cold Spring Harbor Laboratory, Cold Spring Harbor, N.Y. (1988)).

Once the antibodies have been obtained, for example, once individual B cells have been identified and/or monoclonal antibodies have been produced, the sequences encoding the variable regions of these antibodies can be obtained. The variable region sequences can for example be obtained by first sequencing the antibody protein produced by the hybridoma, B-cell or phage and determining the encoding nucleic acid sequence. In one embodiment, the immunoglobulin variable region (VH and VL) DNA or cDNA may be sequenced instead. Where the antibody is derived from a hybridoma cell line or isolated B-cell, the cDNAs encoding the variable regions may be amplified using PCR by for example the methods described in Babcook et al. (*Proc. Natl. Acad. Sci. USA*, 93:7843-7848 (1996)), and in PCT Publication No. WO 92/02551.

The presently disclosed and claimed inventive concept(s) is directed to a new induced luminescence immunoassay architecture that provides improved sensitivity over prior art induced luminescence immunoassays while still maintaining the prior art assay's dynamic range. This new immunoassay architecture can be utilized in the development of new induced luminescence immunoassays for various analytes (including, but not limited to cTnI) and is adaptable for central laboratory and/or POC use. In this new assay architecture, two detection antibodies are utilized in the sandwich assay to replace the single detection antibody used in the current cTnI assay architecture. The combination of one higher affinity antibody with another antibody that exhibits less sensitivity but greater dynamic range when compared to the higher affinity antibody solves the sensitivity and dynamic range issues of the current assay architecture.

FIG. 1 demonstrates the increased sensitivity and dynamic range of the presently disclosed and claimed inventive concept(s) over the prior art. In FIG. 1, dose response curves are depicted for two prior art immunoassays and compared to the assay of the presently disclosed and claimed inventive concept(s) for a particular non-limiting analyte, cTnI. The dose response curve represented by the circular data points represents the current commercial cTnI assay, while the dose response curve represented by square data points represents the assay that uses the higher sensitivity anti-cTnI antibody. As can be seen, a plateau is observed in the upper dynamic range for the assay using the high sensitivity anti-cTnI antibody, while sensitivity is lost in the lower dynamic range of the current commercial cTnI assay. In contrast, the dose response curve represented by the triangular data points is derived from the presently disclosed and claimed cTnI assay architecture that utilizes dual detection antibodies. In comparison to the dose response curves of the prior art cTnI assay architectures that utilize single detection antibodies, the new cTnI architecture provides not only the required cTnI assay sensitivity but also the required cTnI assay dynamic range.

Figure 2A:
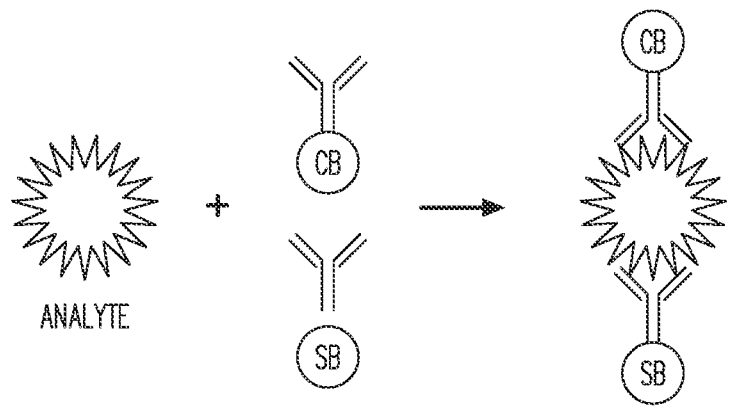
FIGS. 2A and 2B illustrate two embodiments of induced luminescence immunoassay architectures of the prior art.
Figure 2B:
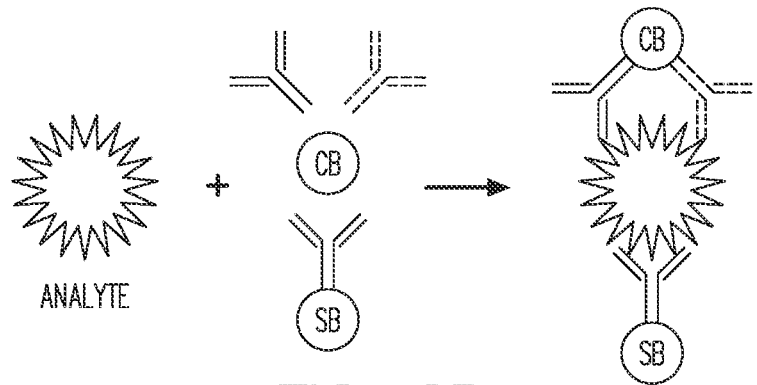
Figure 3:
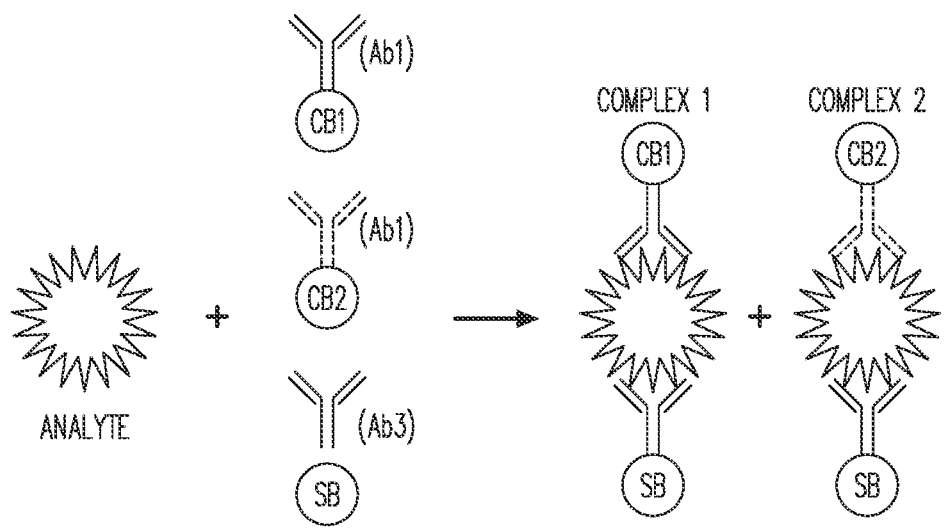
FIG. 3 illustrates an induced luminescence immunoassay architecture constructed in accordance with the presently disclosed and claimed inventive concept(s).

FIGS. 2A, 2B, and 3 provide a comparison of the induced luminescence immunoassay architecture of the presently disclosed and claimed inventive concept(s) to prior art assay architectures. FIG. 2A illustrates a prior art immunoassay architecture that includes a single detection antibody (shown as associated with a chemibead (CB) prior to incubation with the sample containing the analyte) and a single capture antibody (shown as capable of association with a sensibead (SB) during the incubation step). In FIG. 2B, another prior art immunoassay architecture is depicted; in this structure, dual detection antibodies are utilized instead of the single detection antibody in FIG. 2A (wherein both of the detection antibodies are capable of association with a single CB). However, this assay architecture requires that the three antibodies (i.e., both detection antibodies and single capture antibody) must all bind to a single analyte for detection thereof.

In contrast, and as shown in FIG. 3, the assay structure of the presently disclosed and claimed inventive concept(s) utilizes two detection antibodies (Ab1 and Ab2, illustrated as associated with CB1 and CB2, respectively) that compete with one another for binding to an analyte. That is, the two detection antibodies bind to epitopes that at least partially overlap, whereby the two detection antibodies cannot both bind to a single analyte molecule. One of the detection antibodies (Ab1) may possess high sensitivity with limited dynamic range, while the other detection antibody (Ab2) may exhibit a lower level of sensitivity with a greater dynamic range. The use of these two detection antibodies in this manner results in an immunoassay that exhibits a desired sensitivity level over a sufficient dynamic range and detection limit, as shown in FIG. 1.

Turning now to particular embodiments of the presently claimed and disclosed inventive concept(s), assay compositions as well as kits and devices containing same and methods of production and use thereof are disclosed. In some assay embodiments, signal producing system (sps) members comprise a sensitizer such as, for example, a photosensitizer, and a chemiluminescent composition, where activation of the sensitizer results in a product that activates the chemiluminescent composition. One sps member usually generates a detectable signal that relates to the amount of bound and/or unbound sps member, i.e., the amount of sps member bound or not bound to the analyte being detected or to an agent that reflects the amount of the analyte to be detected. An exemplary embodiment of an assay platform on which the presently disclosed and claimed inventive concept(s) is based is the induced luminescence immunoassay (LOCI®). The induced luminescence immunoassay is described in U.S. Pat. No. 5,340,716.

The presently disclosed and claimed inventive concept(s) includes a composition containing a chemiluminescent detection system. In certain embodiments, the composition includes at least three components. The first component comprises a composition that includes a singlet-oxygen activatable chemiluminescent compound and a first antibody or binding fragment thereof associated therewith, wherein the first antibody or binding fragment thereof is a detection antibody that specifically binds to a first epitope of the analyte whereby the singlet-oxygen activatable chemiluminescent compound is capable of indirectly binding to the analyte via the first antibody or binding fragment thereof. The second component comprises a composition that includes a singlet-oxygen activatable chemiluminescent compound and a second antibody or binding fragment thereof associated therewith, wherein the second antibody or binding fragment thereof is a detection antibody that specifically binds to a second epitope of the analyte whereby the singlet-oxygen activatable chemiluminescent compound is capable of indirectly binding to the analyte via the second antibody or binding fragment thereof, and wherein the first and second epitopes at least partially overlap such that the first and second antibodies or binding fragments thereof cannot both bind to a single analyte molecule. The third component comprises a composition that includes a third antibody or binding fragment thereof, the third antibody or binding fragment thereof being a capture antibody that specifically binds to a third epitope of the analyte that does not overlap with the first and second epitopes, whereby a single analyte molecule can bind the third antibody or binding fragment thereof and one of the first and second antibodies or binding fragments thereof, and wherein the third antibody or binding fragment thereof is capable of association with a sensitizer capable of generating singlet oxygen in its excited state, whereby association of the third antibody or binding fragment thereof with the sensitizer allows for the indirect binding of the sensitizer to the analyte.

The first, second, and third epitopes may be all linear epitopes and thus recognize linear portions of the amino acid sequence of the analyte. Alternatively, the first, second, and third epitopes may be all conformational epitopes or a mixture of linear and conformational epitopes. That is, the first epitope may be a linear epitope, while the second epitope may be a conformational epitope (or vice versa); in this manner, the first and second antibodies/binding fragments may not necessarily recognize overlapping portions of the linear amino acid sequence of the analyte; instead, the two antibodies/binding fragments may recognize overlapping portions of the tertiary structure of the amino acid sequence of the analyte.

In certain embodiments, the third component may further include the sensitizer associated with the third antibody or binding fragment thereof. Alternatively, the composition may further include a fourth component that includes the sensitizer.

A sensitizer is a molecule, usually a compound, for generation of a reactive intermediate such as, for example, singlet oxygen, for activation of a chemiluminescent compound. In some embodiments, the sensitizer is a photosensitizer. Other sensitizers that can be chemi-activated (by, e.g., enzymes and metal salts) include, by way of example and not limitation, other substances and compositions that can produce singlet oxygen with or, less preferably, without activation by an external light source. For example, certain compounds have been shown to catalyze the conversion of hydrogen peroxide to singlet oxygen and water. Non-limiting examples of other sensitizer substances and compositions include oxides of the alkaline earth metals Ca, Sr, and Ba; derivatives of elements of groups 3A, 4A, 5A, and 6A in $d^0$ configuration; oxides of actinides and lanthanides; and oxidizers $ClO^-$, $BrO^-$, $Au^{3+}$, $IO_3^-$, and $IO_4^-$; and in particular, molybdate, peroxomolybdate, tungstate, and peroxotungstate ions, and acetonitrile. The following references provide further disclosure regarding sensitizer substances and compositions that also fall within the scope of the presently disclosed and claimed inventive concept: Aubry, *J. Am. Chem. Soc.*, 107:5844-5849 (1985); Aubry, *J. Org. Chem.*, 54:726-728 (1989); Böhme and Brauer, *Inorg. Chem.*, 31:3468-3471 (1992); Niu and Foote, *Inorg. Chem.*, 31:3472-3476 (1992); Nardello et al., *Inorg. Chem.*, 34:4950-4957 (1995); Aubry and Bouttemy, *J. Am. Chem. Soc.*, 119:5286-5294 (1997); and Almeida et al., *Anal. Chim. Acta*, 482:99-104 (2003).

Also included within the scope of photosensitizers are compounds that are not true sensitizers but which on excitation by heat, light, ionizing radiation, or chemical activation will release a molecule of singlet oxygen. Members of this class of compounds include, for example, the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

A photosensitizer is a sensitizer for activation of a photoactive compound, for example, by generation of singlet oxygen by excitation with light. The photosensitizers are photoactivatable and include, e.g., dyes and aromatic compounds, and are usually compounds comprised of covalently bonded atoms, usually with multiple conjugated double or triple bonds. The compounds should absorb light in the wavelength range of 200 to 1,100 nm, or 300 to 1,000 nm, or 450 to 950 nm, with an extinction coefficient at its absorbance maximum greater than 500 $M^{-1}$ $cm^{-1}$, or greater than 5,000 $M^{-1}$ $cm^{-1}$, or greater than 50,000 $M^{-1}$ $cm^{-1}$, at the excitation wavelength. Photosensitizers should be relatively photostable and, preferably, not react efficiently with singlet oxygen. Examples of photosensitizers, by way of illustration and not limitation, include acetone, benzophenone, 9-thioxanthone, eosin, 9,10-dibromoanthracene, methylene blue, metallo-porphyrins, such as hematoporphyrin, phthalocyanines, chlorophylls, rose bengal, and buckminsterfullerene, for example, and derivatives of these compounds.

A chemiluminescent compound (chemiluminescer) is a compound that is chemically activatable and, as a result of such activation, emits light at a certain wavelength. Examples of chemiluminescers, by way of illustration and not limitation, include olefins capable of reacting with singlet oxygen or a peroxide to form hydroperoxides or dioxetanes, which can decompose to ketones or carboxylic acid derivatives; stable dioxetanes which can decompose by the action of light; acetylenes which can react with singlet oxygen to form diketones; hydrazones or hydrazides that can form azo compounds or azo carbonyls such as luminol; and aromatic compounds that can form endoperoxides, for example. As a consequence of the activation reaction, the chemiluminescers directly or indirectly cause the emission of light.

In certain embodiments, the singlet oxygen-activatable chemiluminescent compound may be a substance that undergoes a chemical reaction with singlet oxygen to form a metastabile intermediate species that can decompose with the simultaneous or subsequent emission of light. The composition comprising the singlet oxygen-activatable chemiluminescent compound may associate with the target analyte by any method known in the art; for example but not by way of limitation, the composition may have a second analyte-specific binding partner associated therewith that allows for the indirect association of the chemiluminescent compound to the target analyte. The composition comprising the chemiluminescent compound may be directly excited by the activated chemiluminescent compound; alternatively, the composition may further comprise at least one fluorescent molecule that is excited by the activated chemiluminescent compound. Particular, non-limiting examples of chemiluminescent compounds and photosensitizers that may be utilized in accordance with the presently disclosed and claimed inventive concept(s) are set forth in U.S. Pat. No. 5,340,716 (Ullman, et al.).

The presently disclosed and claimed compositions include the presence of two singlet oxygen activatable chemiluminescent compositions, and any of the singlet oxygen activatable compositions described herein above or otherwise contemplated herein may function as the first and second singlet oxygen activatable compositions. In certain embodiments, it may be desirable for the two singlet oxygen activatable chemiluminescent compositions to be the same singlet oxygen activatable chemiluminescent composition. For example, the same singlet oxygen activatable chemiluminescent composition was associated with both detection antibodies/binding fragments in the assay graphically depicted in FIG. 1, and thus the signal was detected at a single wavelength. In other embodiments, it may be desirable for the two singlet oxygen activatable compositions to be different from one another. When the compositions differ from one another, the binding of the first and second antibodies/binding fragments can be detected at different wavelengths. For example, a first wavelength could be utilized to detect the low end of the curve, and a different wavelength utilized to detect the high end of the curve.

Sensitizers utilized in accordance with the presently disclosed and claimed inventive concept(s) may be capable of indirectly binding to the target analyte via an association with streptavidin. In this manner, biotin is associated with a first analyte-specific binding partner, and the binding of streptavidin and biotin, in combination with the binding of the first analyte-specific binding partner to the target analyte, results in the indirect association of the sensitizer to the target analyte. In one non-limiting example, the sensitizer may be a photosensitizer, such that the sensitizer is activated by irradiation with light.

In certain embodiments, the first antibody/binding fragment and the second antibody/binding fragment exhibit different affinities for the analyte. For example, one of the two antibodies/binding fragments may have a lower affinity for the analyte, while the other antibody/binding fragment has a higher affinity for the analyte. In a particular, non-limiting example, the first antibody/binding fragment may be considered a low affinity antibody that specifically binds to the analyte with a dissociation constant in a range of from $10^{-6}$ M to $10^{-10}$ M, and the second antibody/binding fragment may be considered a high affinity antibody that specifically binds to the analyte with a dissociation constant in a range of from $10^{-10}$ M to $10^{-13}$ M.

Any ratio of high affinity antibody/binding fragment to low affinity antibody/binding fragment may be utilized, so long as the assay is able to function in accordance with the presently disclosed and claimed inventive concept(s) and provide the desired linearity and dynamic range. In particular non-limiting embodiments, the high affinity antibody/binding fragment may be present as about 5% to about 20% of the combination of the two detection antibodies/binding fragments, while the low affinity antibody/binding fragment may be present as about 80% to about 95% of the total detection antibodies present. Particular non-limiting examples of high affinity antibody/fragment to low affinity antibody/fragment ratios that may be utilized include about 5% (high) to about 95% (low), about 10% (high) to about 90% (low), and about 20% (high) to about 80% (low).

The first, second, and third antibodies or binding fragments thereof may be provided in any form that allows these antibodies/binding fragments to function in accordance with the presently disclosed and claimed inventive concept(s). For example, each of the first, second, and third antibodies/binding fragments may be a polyclonal antibody/binding fragment or a monoclonal antibody/binding fragment. In addition, any combination of different types of antibodies/binding fragments may be utilized in accordance with the presently disclosed and claimed inventive concept(s). For example, the first and second antibodies/binding fragments may be monoclonal antibodies/binding fragments, while the third antibody/binding fragment is a polyclonal antibody/binding fragment. Alternatively, the first and second antibodies/binding fragments may be polyclonal antibodies/binding fragments, while the third antibody/binding fragment is a monoclonal antibody/binding fragment. In yet another alternative, one of the first and second antibodies/ binding fragments may be a polyclonal antibody/binding fragment, while the other is a monoclonal antibody/binding fragment. In this example, the third antibody/binding fragment may be polyclonal or monoclonal.

The antibodies may be specific for any analyte for which detection is desired in this manner. Non-limiting examples of analytes contemplated herein include, but are not limited to, troponins, such as cardiac Troponin I (cTnI), CKMB, Myoglobin, Myeloperoxidase, β-hCG, BNP, NT-proBNP, PCT, CRP, and iPHT, the like.

When the analyte to be detected is cTnI, the three antibodies may recognize any three epitopes in the cTnI molecule, so long as the epitopes are positioned as described herein above. That is, the first and second epitopes must at least partially overlap one another such that the first and second antibodies or binding fragments thereof cannot both bind to a single analyte molecule; in addition, the third epitope must not overlap with either the first epitope or the second epitope, whereby the third antibody or binding fragment thereof can bind to a single analyte molecule to which either the first or second antibody or binding fragment thereof is already bound. The entire 210 amino acid sequence of cTnI has been assigned SEQ ID NO:1 herein.

Figure 4:
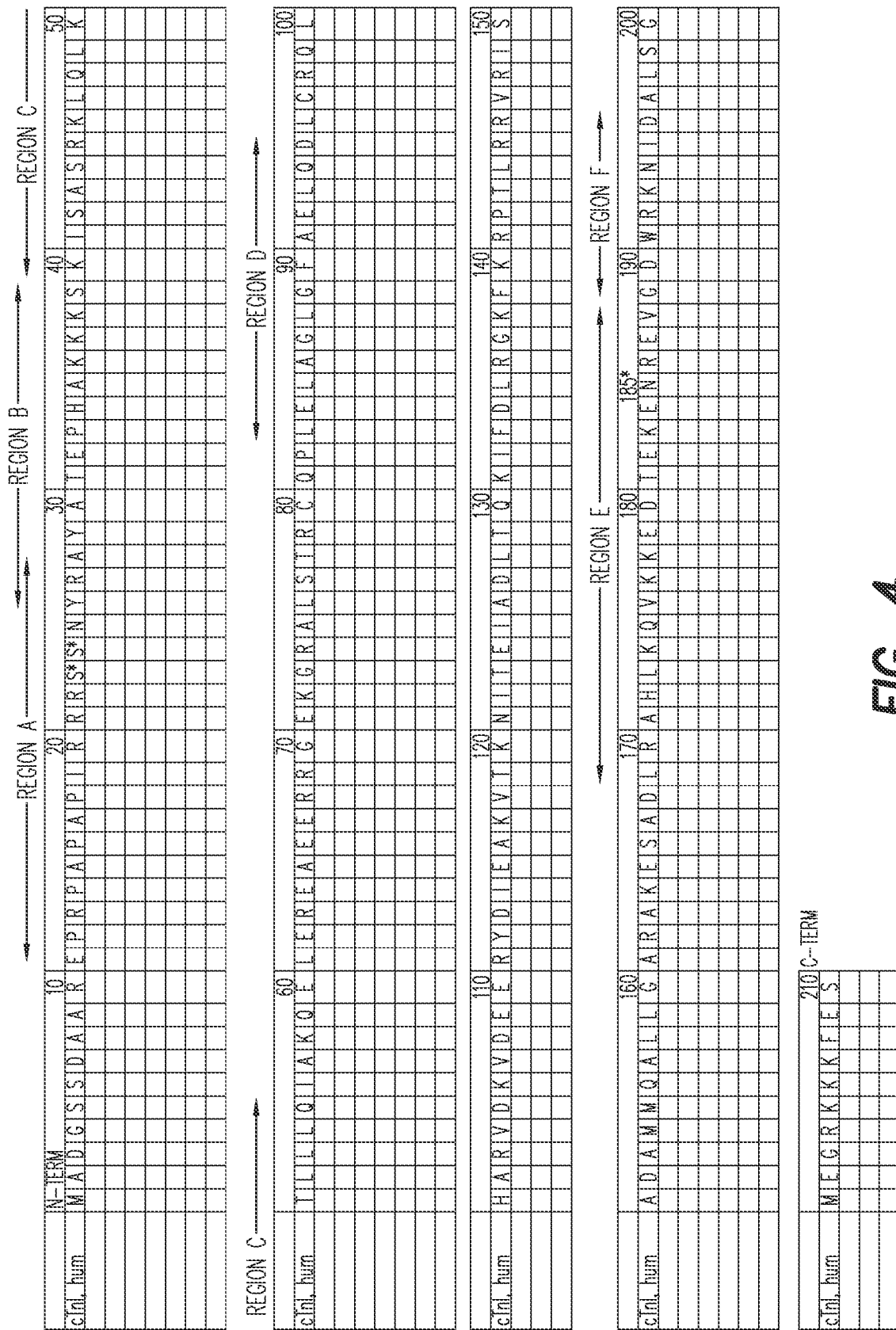
FIG. 4 contains a map of various epitope regions of cTnI.

FIG. 4 contains a map of various epitope regions in the cTnI sequence, illustrating some of the various epitopes that may be utilized in accordance with the presently disclosed and claimed inventive concept(s). In certain non-limiting embodiments of the presently disclosed and claimed inventive concept(s), the analyte to be detected is cTnI, and the first and second antibodies/binding fragments specifically bind to overlapping epitopes within one of regions A, B, C, D, E, and F (i.e., SEQ ID NOS: 2-7, respectively) of FIG. 4, while the third antibody/binding fragment thereof specifically binds to an epitope within a different region. For example but not by way of limitation: (a) the first and second antibodies/binding fragments bind to overlapping epitopes within region A (SEQ ID NO:2), and the third antibody/binding fragment specifically binds to an epitope within one of regions B-F (i.e., one of SEQ ID NOS: 3-7); (b) the first and second antibodies/binding fragments bind to overlapping epitopes within region B (SEQ ID NO:3), and the third antibody/binding fragment specifically binds to an epitope within one of regions A and C-F (i.e., one of SEQ ID NOS: 2 and 4-7); (c) the first and second antibodies/binding fragments bind to overlapping epitopes within region C (SEQ ID NO:4), and the third antibody/binding fragment specifically binds to an epitope within one of regions A-B and D-F (i.e., one of SEQ ID NOS: 2-3 and 5-7); (d) the first and second antibodies/binding fragments bind to overlapping epitopes within region D (SEQ ID NO:5), and the third antibody/binding fragment specifically binds to an epitope within one of regions A-C and E-F (i.e., one of SEQ ID NOS: 2-4 and 6-7); (e) the first and second antibodies/binding fragments bind to overlapping epitopes within region E (SEQ ID NO:6), and the third antibody/binding fragment specifically binds to an epitope within one of regions A-D and F (i.e., one of SEQ ID NOS: 3-5 and 7); and (f) the first and second antibodies/binding fragments bind to overlapping epitopes within region F (SEQ ID NO:7), and the third antibody/binding fragment specifically binds to an epitope within one of regions A-E (i.e., one of SEQ ID NOS:2-6). In particular non-limiting examples, the first and second antibodies/binding fragments bind to overlapping epitopes within region A or region B (SEQ ID NO:2 or SEQ ID NO:3, respectively), and the third antibody/binding fragment specifically binds to an epitope within region C (SEQ ID NO:4).

Additional non-limiting examples of cTnI epitopes/antibody combinations utilized in cTnI immunoassays in accordance with the presently disclosed and claimed inventive concept(s) include the following: (i) the first and second antibodies/binding fragments thereof specifically bind to any of the epitopes of SEQ ID NOS:8, 9, and 11, while the third antibody or binding fragment thereof specifically binds to the epitope of SEQ ID NO:10; (i) the first and second antibodies/binding fragments thereof specifically bind to the epitopes of SEQ ID NOS:8 and 9, while the third antibody or binding fragment thereof specifically binds to the epitope of SEQ ID NO:10; (ii) the first and second antibodies/binding fragments thereof specifically bind to the epitopes of SEQ ID NOS:9 and 11, while the third antibody or binding fragment thereof specifically binds to the epitope of SEQ ID NO:10; and (iii) the first and second antibodies/binding fragments thereof specifically bind to the epitopes of SEQ ID NOS:12 and 13, while the third antibody or binding fragment thereof specifically binds to the epitope of SEQ ID NO:14. Specific combinations of epitopes are illustrated in FIGS. 15-17 and will be discussed in detail in the Examples below.

Figure 18:
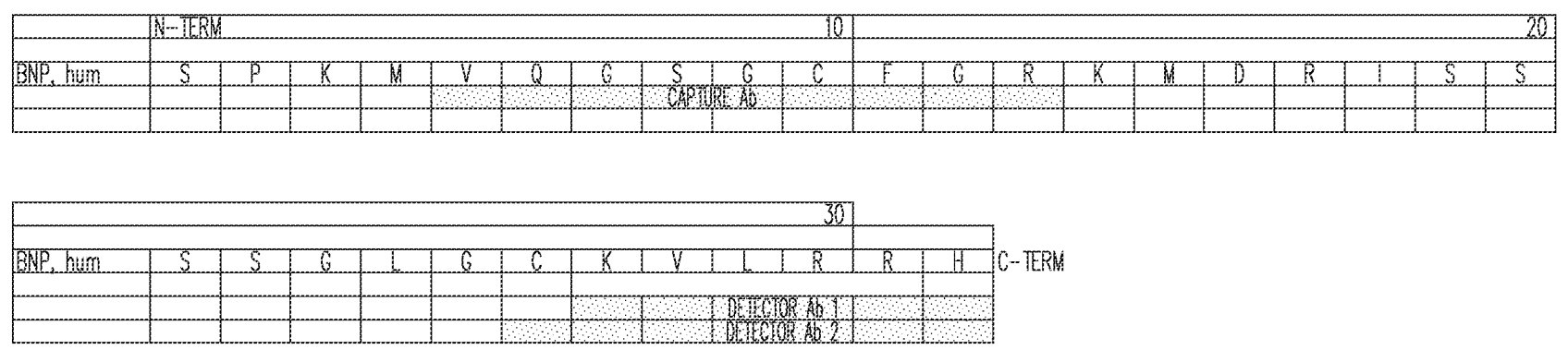

When the analyte to be detected is B-type natriuretic peptide (BNP), the three antibodies may recognize any three epitopes in the BNP molecule, so long as the epitopes are positioned as described herein above (i.e., first and second epitopes at least partially overlapping one another and the third epitope not overlapping either of the first and second epitopes). A 32 amino acid sequence of BNP has been assigned SEQ ID NO:15 and is shown in FIG. 18, along with a non-limiting example of a combination of epitopes that may be utilized in accordance with the presently disclosed and claimed inventive concept(s). In the non-limiting example depicted in FIG. 18 (and as described in detail in the Example section below), the first and second antibodies/binding fragments thereof may specifically bind to the epitopes of SEQ ID NOS:16 and 17, while the third antibody or binding fragment thereof specifically binds to the epitope of SEQ ID NO:18.

The reagents of the compositions/kits/methods may be provided in any form and/or formulation that allows them to function in accordance with the presently disclosed and claimed inventive concept(s). For example but not by way of limitation, the components may be in the form of a bead or similar formulation. In addition, in certain embodiments, it may be desirable to dispose the reagents in the form of single use lyophilized reagents. The use of dried reagents in microfluidics devices is described in detail in patent application publication WO 2013/078130 A1.

In certain embodiments, multiple components may be disposed together in a single bead or formulation and/or lyophilized in a single particle. For example but not by way of limitation, a single bead may include the first and second components; that is, a single bead may contain both the first and second antibodies/binding fragments as well as the singlet-oxygen activatable chemiluminescent compound(s) associated with the antibodies/binding fragments. The single bead containing both components may then be lyophilized into a single particle or disposed in another formulation.

In addition, two or more components that are disposed in separate beads/formulations may be lyophilized together. For example but not by way of limitation, the first and second components (containing the first and second antibodies/binding fragments associated with singlet-oxygen activatable chemiluminescent compound(s))—may be lyophilized together. In another non-limiting example, the first and second components (containing the first and second antibodies/binding fragments associated with singlet-oxygen activatable chemiluminescent compound(s)) and the third component (containing the third antibody/binding fragment) may be lyophilized together as a single particle. In addition, a single lyophilized particle may contain combinations of multiple types of beads/formulations; that is, a single lyophilized particle may contain a mixture of: (a) a single bead containing both first and second components; (b) a bead containing only the first component; and (c) a bead containing only the second component.

Any of the compositions described above or otherwise contemplated herein may further include additional components, such as but not limited to, diluents, wash solutions, and/or excipients (utilized for the reconstitution of lyophilized reagents). In addition, any of the compositions described herein above or otherwise contemplated herein may also include a microfluidics device in which one or more of the above-described components are disposed.

The presently disclosed and claimed inventive concept(s) further includes kits useful for conveniently performing an assay for the determination of an analyte; the kit may contain any combination of the above-described components/reagents (including any of the embodiments of compositions described herein above); in addition, the kit may further contain other reagent(s) for conducting any of the particular assays described or otherwise contemplated herein. The nature of these additional reagent(s) will depend upon the particular assay format, and identification thereof is well within the skill of one of ordinary skill in the art.

The components/reagents may each be disposed in separate containers/compartments, or various components/reagents can be combined in one or more containers/compartments, depending on the competitive nature of the antibody binding constants/efficiencies and/or the stability of the components/reagents. The kit can further include other separately packaged reagents for conducting an assay, such as additional sbp members, sps members and ancillary reagents, for example. In addition, the kit may include a microfluidics device in which the components/reagents are disposed.

The relative amounts of the various components/reagents in the kits can vary widely to provide for concentrations of the components/reagents that substantially optimize the reactions that need to occur during the assay methods and further to optimize substantially the sensitivity of an assay. Under appropriate circumstances one or more of the components/reagents in the kit can be provided in a dry form, such as a lyophilized particle (including but not limited to, spheres, microtablets, powders, microspots, etc.), and the kit may further include excipient(s) for dissolution of the dried reagents; in this manner, a reagent solution having the appropriate concentrations for performing a method or assay in accordance with the presently disclosed and claimed inventive concept(s) can be obtained from these components. Positive and/or negative controls may be included with the kit. The kit can further include a set of written instructions explaining how to use the kit. A kit of this nature can be used in any of the methods described or otherwise contemplated herein.

The presently disclosed and claimed inventive concept(s) is further directed to a microfluidics device in which the compositions described herein above are disposed. The microfluidics device may have one or more manual functions associated therewith (i.e., wherein pipetting is required for addition of one or more reagents and/or movement of a mixture between two compartments); alternatively, the microfluidics device may be a fully automatic, closed system in which the necessary reagents are disposed in various compartments during construction of the microfluidics device (wherein the various compartments are in continuous fluidic communication (or are capable of being in continuous fluidic communication)), and thus no manual manipulation of the sample and/or reagent(s) is required for performance of the assay after the sample is added to the microfluidics device. The microfluidics device comprises one or more compartments containing the three or four components described herein above (i.e., the three antibody-containing compositions with or without the sensitizer; when the sensitizer is present, it may be provided alone, or it may be associated with the third antibody-containing composition). The device may be provided with any number of compartments, any arrangement of compartments, and any distribution of the three or four components there between, so long as the device is able to function in accordance with the presently disclosed and claimed inventive concept(s); non-limiting examples of device structure are provided in the Figures for illustrative purposes only. When provided with multiple compartments, the compartments may be completely separated from one another, or one or more compartments may be capable of being in fluidic communication with one another.

The microfluidics device may further include a sample application chamber and/or an inlet channel in which a sample may be applied/disposed. The sample application chamber/inlet channel may be capable of being in fluidic communication with the one or more compartments of the microfluidics device. In addition, when the microfluidics device is provided with both a sample application chamber and an inlet channel, the sample application chamber may be capable of being in fluidic communication with the inlet channel, while the inlet channel may be capable of being in fluidic communication with the one or more compartments in which the reagents are disposed.

A sample may be applied directly in the compartment containing the assay reagents, or the sample may pass through the sample application chamber/inlet channel before entering the compartment(s) containing the assay reagent(s). When the sample passes through one or more components before reaching the assay compartment(s), substantially all of the sample may pass through and thus remain substantially intact upon reaching the assay compartment(s). Alternatively, only portions of the sample may reach the assay compartment. In one embodiment, this may occur simply because of size, weight, and/or volume restrictions in the compartments upstream of the assay compartment(s); in another embodiment, the microfluidics device may contain one or more structure(s) present in the sample application chamber, the inlet channel, a compartment upstream of the assay compartment(s), and/or any connection therebetween that allows for separation of certain components of a sample from a whole sample and/or delivery of said components to the assay compartment(s).

In one embodiment, the three or four reagents are disposed in a single compartment of the microfluidics device. In another embodiment, the microfluidics device may contain at least two compartments; the first compartment may contain the first three compositions (i.e., first and second antibodies/binding fragments associated with singlet-oxygen activatable compositions and the third antibody/binding fragment) while the second compartment contains the sensitizer. In addition, this microfluidics device comprising two compartments may further comprise an inlet channel through which a sample may be applied; in this configuration, the first compartment may be capable of being in fluidic communication with the inlet channel, and the second compartment may be capable of being in fluidic communication with at least one of the inlet channel and the first compartment. In another embodiment, the microfluidics device may contain at least three compartments; the first, second, and third compartments may contain the first, second, and third components, respectively. In addition, it may be desirable that the first antibody/binding fragment (present in the first component) bind with high affinity to the target analyte, while the second antibody/binding fragment (present in the second component) bind with low affinity to the target analyte. In this manner, the higher affinity antibody/binding fragment comes into contact with the analyte before the lower affinity antibody/binding fragment.

Any of the compartments of the microfluidics device may be sealed to maintain reagent(s) disposed therein in a substantially airtight environment until use thereof; for example, compartments containing lyophilized reagent(s) may be sealed to prevent any unintentional reconstitution of the reagent(s). The inlet channel and a compartment, as well as two compartments, may be described as being "capable of being in fluidic communication" with one another; this phrase indicates that the compartment(s) may still be sealed, but the two compartments are capable of having fluid flow there between upon puncture of a seal formed therein or there between.

The microfluidics devices of the presently disclosed and claimed inventive concept(s) may be provided with any other desired features known in the art or otherwise contemplated herein. For example, but not by way of limitation, the microfluidics devices of the presently disclosed and claimed inventive concept(s) may further include a read chamber; the read chamber may be a compartment containing one or more of the assay components, or the read chamber may be in fluidic communication with one or more compartments containing the assay reagent(s). The microfluidics device may further include one or more compartments containing other solutions, such as but not limited to, wash solutions, diluents, excipients, interference solutions, positive controls, negative controls, quality controls, any combination thereof, and the like. For example, the microfluidics device may include one or more compartments containing a diluent, and these compartment(s) may be capable of being in fluidic communication with any other compartment(s) of the device. In another example, the microfluidics device may further include one or more compartments containing at least one excipient for reconstitution of one or more lyophilized reagents, and the compartment(s) may be capable of being in fluidic communication with any other compartment(s) of the device (such as the compartment containing the lyophilized reagent). Further, the microfluidics device may further include one or more compartments containing a wash solution, and the compartment(s) may be capable of being in fluidic communication with any other compartment(s) of the device.

In addition, any of the kits/microfluidics devices described or otherwise contemplated herein may include multiple assays multiplexed in a single kit/device. When multiple assays are present, both of the assays may be constructed and function as described herein. Alternatively, an assay as described herein may be multiplexed with any other type of induced luminescence immunoassay known in the art (such, as but not limited to, the LOCI® immunoassay technology described in U.S. Pat. No. 5,340,716 and in U.S. Provisional Application Nos. 61/787,735; 61/788,194; and 61/788,692; all filed Mar. 15, 2013, that is capable of being contained within the kits/microfluidics devices of the presently disclosed and claimed inventive concept(s). When multiple assays are present in a single kit/microfluidics device, the two or more assays may be run simultaneously and/or sequentially (including wholly or partially sequentially). When two or more assays are run simultaneously, it may be desired to utilize two different singlet oxygen activatable chemiluminescent compounds. When two or more assays are run in parallel (whether wholly or partially sequentially), the same singlet oxygen activatable chemiluminescent compound may be utilized in both assays, and the two assays are read at different time points.

When multiple assays are present in a single microfluidics device, multiple inlet channels may be connected to the sample application chamber. In certain embodiments, a portion of the sample may be passed from the sample application chamber to the multiple inlet channels without regard for the content thereof. Alternatively, structure(s) may be present in the sample application chamber, the inlet channels, and/or the connection therebetween that allow for separation of certain components from the whole sample and delivery of said components to the different assays. A non-limiting example of a sample distribution device that may be utilized in accordance with the presently disclosed and claimed inventive concept(s) is described in detail in Provisional Application No. 61/790,580, filed Mar. 15, 2013, entitled "Microfluidic Distributing Device."

The presently disclosed and claimed inventive concept(s) is further directed to a method for detecting the presence and/or concentration of a target analyte in a sample (such as but not limited to, whole blood, lysed whole blood cells, or red blood cells). In one embodiment, the method includes the steps of combining, either simultaneously or wholly or partially sequentially: a sample suspected of containing the specific analyte; the two compositions comprising singlet-oxygen activatable chemiluminescent compounds associated with the first and second antibodies/binding fragments; the third composition containing the third antibody/binding fragment, and the sensitizer. The mixture is incubated under conditions that allow the three antibodies/binding fragments to bind to analyte within the sample; this results in the formation of two sandwich complexes: a first sandwich complex comprising an analyte molecule having the first antibody/binding fragment-containing composition and the third antibody/binding fragment-containing composition bound thereto, and a second sandwich complex comprising another analyte molecule having the second antibody/binding fragment-containing composition and the third antibody/binding fragment-containing composition bound thereto. If the sensitizer is not already associated with the third antibody/binding fragment-containing composition, incubation of the mixture also results in association of sensitizer with the first and second sandwich complexes via the third antibody/binding fragment-containing composition present in the sandwich complexes, thus bringing the sensitizer into close proximity to the chemiluminescent compounds of first and second antibody/binding fragment-containing compositions.

The sensitizer is then activated to generate singlet oxygen, wherein activation of the sensitizer present in the first and second sandwich complexes causes the activation of the chemiluminescent compounds present in the first and second sandwich complexes. The amount of chemiluminescence generated by the activated chemiluminescent compounds present in the first and second sandwich complexes is then determined. The binding/incubation, activation, and/or determination steps may optionally be repeated for a desired number of times. The presence and/or concentration of the analyte is detected by analyzing the amount of chemiluminescence so produced, wherein the amount of chemiluminescence is directly proportional to the amount of analyte in the sample.

As mentioned above, the sample and various components of the method are provided in combination (either simultaneously or sequentially). When the sample and various components of the method are added sequentially, the order of addition of the sample/components may be varied; a person having ordinary skill in the art can determine the particular desired order of addition of the sample/different components to the assay. The simplest order of addition, of course, is to add all the materials simultaneously and determine the signal produced therefrom. Alternatively, the sample and each of the components, or groups of components, can be combined sequentially. In certain embodiments, an incubation step may be involved subsequent to addition of sample and/or each component.

When the sensitizer is a photosensitizer, the activation step may be further defined as activating the photosensitizer via irradiation with light. When at least one of the first and second compositions further comprises at least one fluorescent molecule that is excited by the activated chemiluminescent compound, the method may further comprise a step of measuring the amount of light emitted by the fluorescent molecules to determine the amount of analyte in the sample.

The sample may be exposed to a separation step prior to combination with any of the assay reagents. For example but not by way of limitation, it may be desirable to separate plasma, serum, or a specific cell type (such as but not limited to, red blood cells) from whole blood sample prior to commencing the assay, so that components present in the whole blood sample do not affect the sensitivity, dynamic range, and/or detection limit of the assay.

It may be desired to dilute the mixture formed from the incubation/binding step prior to activation of the sensor, and thus the method may further include the step of adding a diluent to the incubated mixture of sample and reagents. There are multiple factors that can contribute to background signal, such as but not limited to: (1) the nonspecific binding of two assay compositions to one another, and (2) the presence of two unattached assay compositions that are simply in close proximity to one another. For these reasons, it may be desirable to dilute the final reaction mixture prior to light exposure to dissociate nonspecifically bound compositions and to increase the mean particle distance between unbound compositions.

Figure 5:
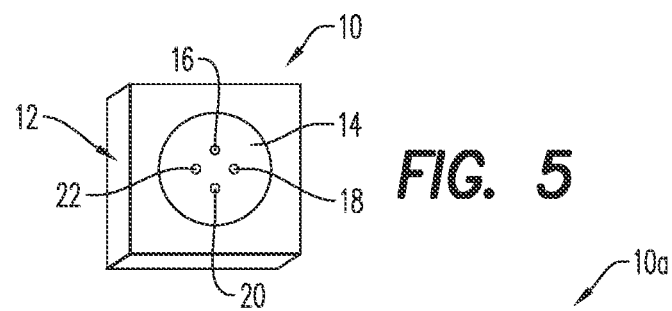
FIG. 5 illustrates a first embodiment of a basic architecture for a microfluidics device constructed in accordance with the presently disclosed and claimed inventive concept(s).
Figure 6:
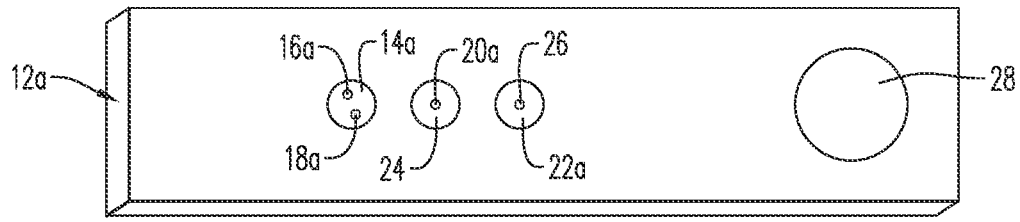
FIG. 6 illustrates another embodiment of a basic architecture for a microfluidics device constructed in accordance with the presently disclosed and claimed inventive concept(s).

Turning now to the particular embodiments shown in the Drawings, FIGS. 5 and 6 depict "open system" microfluidics devices, where one or more manual functions are required for performance of the assay (i.e., pipetting is required for addition of one or more reagents and/or movement of a mixture between two compartments).

FIG. 5 depicts a microfluidics device constructed in accordance with the presently disclosed and claimed inventive concept(s). The microfluidics device is indicated by the general reference numeral 10 and includes a housing 12 that includes a compartment 14. The compartment 14 contains a predetermined amount of each of the first composition 16 (that contains a singlet-oxygen activatable chemiluminescent compound associated with the first antibody/binding fragment), the second composition 18 (that contains a singlet-oxygen activatable chemiluminescent compound associated with the second antibody/binding fragment), and the third composition 20 (that contains the third antibody/binding fragment). The third composition 20 may further include sensitizer that is associated with the third antibody/binding fragment, or the compartment 14 may further contain a predetermined amount of sensitizer 22 that is separate from the third composition 20. In addition, while the four compositions 16, 18, 20, and 22 are depicted as being separate components, two or more of these separate components may be lyophilized together into a single particle.

When using the microfluidics device 10 of FIG. 5, a sample is manually applied (i.e., pipetted) directly into the compartment 14. If a diluent is utilized, the diluent may also be manually applied (i.e., pipetted) into the compartment 14, such as but not limited to, following addition of the sample and/or incubation of the reaction mixture. The compartment 14 may function as both a mixing/incubation chamber and as a read chamber, whereby the sensitizer is activated in the compartment 14 and the chemiluminescence so generated is measured directly from the compartment 14. Alternatively, the compartment 14 may simply function as a mixing and/or incubation chamber, and the reaction mixture may be removed from the compartment 14 and added to another device in which the activation and/or reading steps are performed. That is, the assay may require the use of two devices (chips): the device 10 as well as a separate device with no connection to the device 10. In this manner, the reaction mixture is incubated out of the compartment 14 of the device 10 and transferred to the separate device.

FIG. 6 depicts a microfluidics device 10a that is similar to the microfluidics device 10 of FIG. 5, except as described herein below. The microfluidics device 10a includes a housing 12a that includes a first compartment 14a; however, the housing 12a further comprises a second compartment 24 and a third compartment 26. The first composition 16a, the second composition 18a, the third composition 20a, and the sensitizer 22a may be dispersed between the three compartments 14a, 24, and 26. For purposes of illustration only, the first and second compositions 16a and 18a are depicted as being disposed in the first compartment 14a, while the third composition 20a is disposed in the second compartment 24, and the sensitizer 22a is disposed in the third compartment 26. However, it is to be understood that any order of dispersal of the compositions 16a, 18a, 20a, and 22a (or 16a, 18a, and 20a, when the sensitizer 22a is included in the third composition 20a) between the compartments 14a, 24, and 26 may be utilized, so long as the assay is able to function in accordance with the presently disclosed and claimed inventive concept(s). In addition, while the four compositions 16a, 18a, 20a, and 22a are depicted as being separate components, two or more of the separate components may be lyophilized together into a single particle.

When using the microfluidics device 10a of FIG. 6, a sample is manually applied (i.e., pipetted) directly into the compartment 14a and allowed to incubate with the compositions 16a and 18a disposed therein. The reaction mixture from compartment 14a is then removed from the compartment 14a and applied directly to the compartment 24 and allowed to incubate with the composition 20a. The reaction mixture from compartment 24 is then removed from compartment 24 and applied directly to the compartment 26 and allowed to incubate with the sensitizer 22a. The reaction mixture from compartment 26 is then removed from compartment 26 and applied directly to the read chamber 28, in which the sensitizer 22a is activated in the read chamber 28 and the chemiluminescence so generated is measured directly from the read chamber 28.

It will be understood that the number of incubation/mixing compartments and order of disposal of the assay reagents within the open system microfluidics devices depicted in FIGS. 5 and 6 is for purposes of illustration only, and should not be construed as limiting. While FIGS. 5 and 6 depict microfluidics devices containing one or three incubation/mixing compartments in which the assay reagents are disposed, it will be understood that devices containing one, two, three, or four incubation/mixing compartments in which the assay reagents are disposed are fully contemplated within the scope of the presently disclosed and claimed inventive concept(s). In addition, when the device contains two or more incubation/mixing compartments, the assay reagents may be dispersed between the two or more incubation/mixing compartments in any desired order, so long as the assay can function as described herein. Further, regardless of the number of incubation/mixing compartments present, the final incubation/mixing compartment may also be a read chamber; alternatively, a read chamber may also be present in the microfluidics device in addition to the one, two, three, or four incubation/mixing chambers. Also, the microfluidics device may further contain one or more additional structures, such as but not limited to, an additional compartment in which an excipient and/or diluent may be disposed prior to addition to one or more of the compartments.

FIGS. 7-12 depict "closed system" microfluidics devices in which the necessary assay reagents are disposed in various compartments of the microfluidics devices during construction thereof. These microfluidics devices comprise a fully automatic, closed system in which no manual functions are required for performance of the assay after the sample is added to the microfluidics device.

Figure 7:
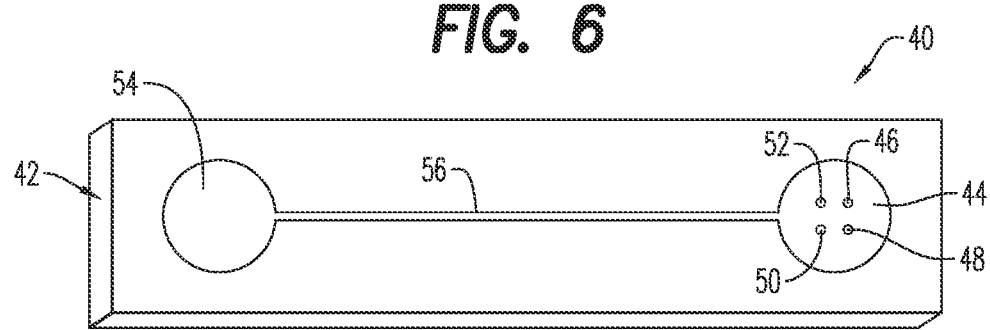
FIG. 7 illustrates another embodiment of a basic architecture for a microfluidics device constructed in accordance with the presently disclosed and claimed inventive concept(s).

FIG. 7 depicts another embodiment of a microfluidics device constructed in accordance with the presently disclosed and claimed inventive concept(s). The microfluidics device 40 includes a housing 42 that includes a compartment 44 containing the first composition 46, the second composition 48, and the third composition 50. The third composition 50 may include the sensitizer associated with the third antibody/binding fragment, or the compartment 44 may further contain a predetermined amount of sensitizer 52 separate from the third composition 50. In addition, while the four compositions 46, 48, 50, and 52 are depicted as being separate components, any of the separate components may be lyophilized together into a single particle.

The housing 42 further includes a sample application chamber 54 and an inlet channel 56 that connects the sample application chamber 44 to the compartment 44. A sample (such as, but not limited to, a blood sample) may be applied to the sample application chamber 54, which is in (or is capable of being in) fluidic communication with the inlet channel 56. The inlet channel 56 is in (or is capable of being in) fluidic communication with the compartment 44. The compartment 44 may function as both a mixing/incubation chamber and as a read chamber.

The inlet channel 56 may simply transfer a portion of the sample to the compartment 44, or the inlet channel 56 may contain one or more structures that allow for separation of certain components from the whole sample (i.e., separation filter(s) that provide for separation of plasma, serum, or red blood cells from a whole blood sample applied to the sample application chamber 54) and/or detection of degradation (such as but not limited to, hemolysis) in the sample.

Figure 8:
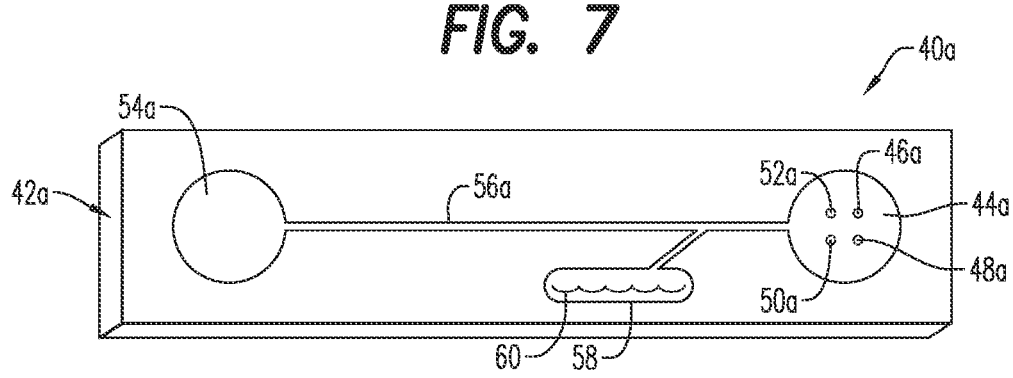
FIG. 8 illustrates another embodiment of a basic architecture for a microfluidics device constructed in accordance with the presently disclosed and claimed inventive concept(s).

Any of the microfluidics devices described or otherwise contemplated herein may be provided with additional compartments containing other reagents/solutions. For example, FIG. 8 depicts a microfluidics device 40a that is similar to the microfluidics device 40 of FIG. 7, except that the microfluidics device 40a further includes a second compartment 58 that is in (or is capable of being in) fluidic communication with the inlet channel 56a and/or the first compartment 44a; the second compartment 58 contains a predetermined amount of at least one reagent 60, such as an excipient, diluent, wash solution, etc. For example but not by way of limitation, when the compositions 50a, 52a, 54a, and/or 56a are in the form of dried reagent(s), the sample itself may be utilized for reconstitution of the dried reagent(s); alternatively, the microfluidics device may be provided with one or more compartments containing excipient that may be in (or may be capable of being in) fluidic communication with the compartment(s) containing said reagent(s).

Any of the compartments of any of the microfluidics devices described or otherwise contemplated herein may be sealed to maintain reagent(s) disposed therein in a substantially air tight and/or substantially light tight environment until use thereof; for example, compartments containing lyophilized reagent(s) may be sealed to prevent any unintentional reconstitution of the reagent and/or exposure of any of the reagents to light. The inlet channel and a first compartment, as well as two compartments, may be described as being "capable of fluidic communication" with one another; this phrase indicates that the compartment(s) may still be sealed, but are capable of having fluid flow there between upon puncture of a seal formed therein.

In addition, it is to be understood that any of the microfluidics devices described or otherwise contemplated herein may further be provided with additional chambers and/or other fluidic circuits. For example, but not by way of limitation, any of the microfluidics devices may additionally contain mixing chamber(s) and/or fluidic circuit(s) that are disposed between two reagent chambers.

Figure 9:
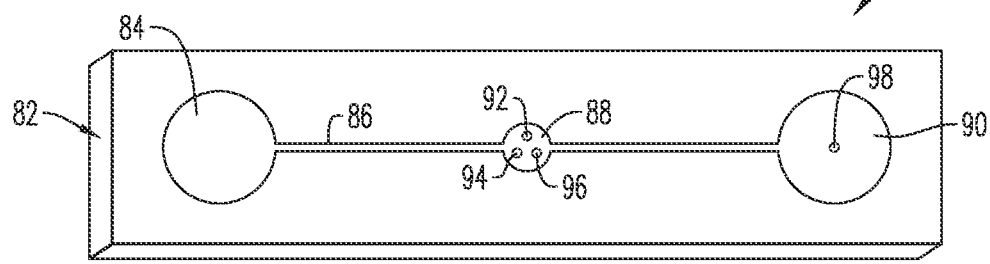
FIG. 9 illustrates another embodiment of a basic architecture for a microfluidics device constructed in accordance with the presently disclosed and claimed inventive concept(s).

FIG. 9 depicts another embodiment of a microfluidics device constructed in accordance with the presently disclosed and claimed inventive concept(s). The microfluidics device is indicated by the general reference numeral 80 and is similar to the microfluidics devices 10, 10a, 40, and 40a of FIGS. 5-8, except that the microfluidics device 80 contains two compartments, and the assay reagents may be split between these two compartments.

The microfluidics device 80 includes a housing 82 that includes a sample application chamber 84, an inlet channel 86, a first compartment 88, and a second compartment 90. A sample (such as, but not limited to, a blood sample) may be applied to the sample application chamber 84, which is in (or is capable of being in) fluidic communication with the inlet channel 86. The inlet channel 86 is in (or capable of being in) fluidic communication with the first compartment 88. The first compartment 88 is illustrated as containing a predetermined amount of each of the first composition 92 and the second composition 94, and may also contain a predetermined amount of the third composition 96. The second compartment 90 is in (or is capable of being in) fluidic communication with the first compartment 88; the second compartment 90 is illustrated as containing a predetermined amount of sensitizer 98. While the third composition 96 is depicted in FIG. 9 as being disposed in the first compartment 88, it should be understood that the third composition 96 may alternatively be disposed in the second compartment 90. In addition, while the third composition 96 and the sensitizer 98 are depicted in FIG. 9 as being two separate components, it will be understood that a single composition may be present in the second compartment 90 that contains both the third composition 96 and the sensitizer 98.

The order of disposal of the reagents 92, 94, 96, and 98 in the compartments 88 and 90 is for the purposes of example only and should not be construed as limiting. The reagents 92, 94, 96, and 98 may be disposed in the compartments 88 and 90 in any desired order. In addition, while the four compositions 92, 94, 96, and 98 are depicted as being separate components, any of the separate components may be lyophilized together into a single particle and disposed in either of the compartments 88 and 90.

The microfluidics device 80 may further be provided with one or more additional compartments containing additional reagents (such as but not limited to, diluents, excipient, wash solution, etc.). When one or more additional compartments are provided, the compartments may be in (or may be capable of being in) fluidic communication with the first compartment 88 and/or the second compartment 90.

Figure 10:
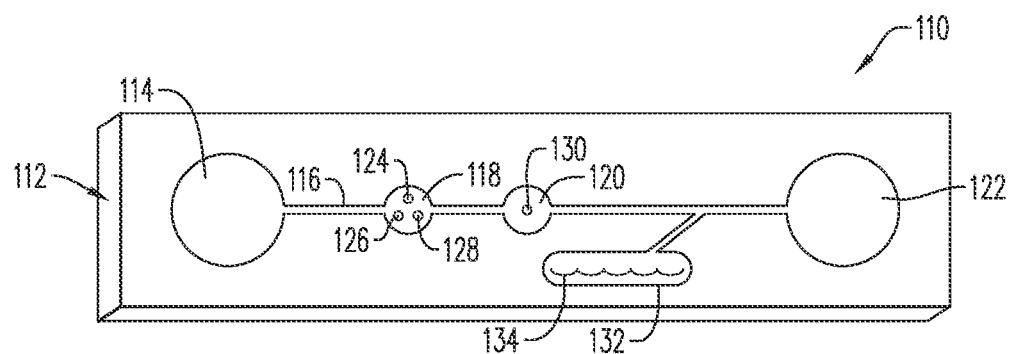
FIG. 10 illustrates yet another embodiment of a basic architecture for a microfluidics device constructed in accordance with the presently disclosed and claimed inventive concept(s).

In certain embodiments, the compartment of a microfluidics device that contains the sensitizer (such as the second compartment 90 of the microfluidics device 80 of FIG. 9) may function as a read chamber. Alternatively, an additional compartment may be present that is in (or is capable of being in) fluidic communication with the sensitizer-containing compartment, and this additional compartment acts as a read chamber. For example, FIG. 10 illustrates a microfluidics device 110 comprising a housing 112 that includes a sample application chamber 114, an inlet channel 116, a first compartment 118, a second compartment 120, a read chamber 122, and an additional compartment 132. A sample (such as, but not limited to, a blood sample) may be applied to the sample application chamber 114, which is in (or is capable of being in) fluidic communication with the inlet channel 116. The first compartment 118 is in (or is capable of being in) fluidic communication with the inlet channel 116, while the second compartment 120 is in (or is capable of being in) fluidic communication with the first compartment 118. The first and second compartments 118 and 120 are illustrated as containing the assay compositions 124, 126, 128, and 130, as described in greater detail herein below. The read chamber 122 is in (or is capable of being in) fluidic communication with the second compartment 120. The additional compartment 132 is in (or is capable of being in) fluidic communication with one or more of the inlet channel 116, the first compartment 118, the second compartment 120, and/or the read chamber 122. The additional compartment 132 contains a predetermined amount of at least one reagent 134, such as an excipient, diluent, wash solution, etc.

For purposes of example only, the first compartment 118 is illustrated as containing a predetermined amount of each of the first composition 124, the second composition 126, and the third composition 128, and the second compartment 120 is illustrated as containing a predetermined amount of sensitizer 130. However, it is to be understood that the four compositions 124, 126, 128, and 130 may be disposed in any order within the microfluidics device 110, so long as the microfluidics device 110 is capable of functioning in accordance with the presently disclosed and claimed inventive concept(s). For example but not by way of limitation, the third composition 128 may alternatively be disposed in the second compartment 120. In addition, while the third composition 128 and the sensitizer 130 are depicted as being two separate components, it will be understood that the third composition 128 and sensitizer 130 may be associated with one another prior to disposal within the microfluidics device 110. Further, while the four compositions 124, 126, 128, and 130 are depicted as being separate components, two or more of the separate components may be lyophilized together into a single particle and disposed in the either of the compartments 118 or 120.

Figure 11:
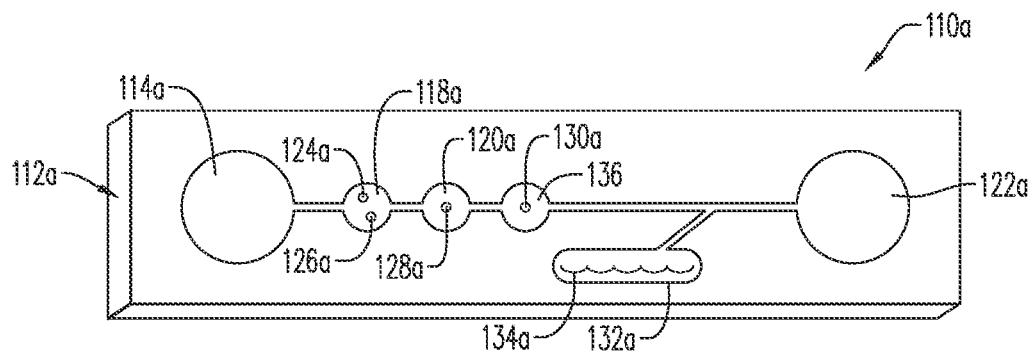
FIG. 11 illustrates a further embodiment of a basic architecture for a microfluidics device constructed in accordance with the presently disclosed and claimed inventive concept(s).

The microfluidics devices 40, 40a, and 80 of FIGS. 7-9 illustrate the disposal of the four assay compositions within a single compartment, whereas the microfluidics device 10 of FIG. 10 illustrates the dispersal of the four assay compositions between two compartments; however, it should be understood that the four assay compositions may be dispersed between three or more compartments. For example, FIG. 11 illustrates a microfluidics device 110a that is similar to the microfluidics device 110 of FIG. 10, except as described herein below. The microfluidics device 110a comprises a housing 112a that includes a sample application chamber 114a, an inlet channel 116a, a first compartment 118a, a second compartment 120a, a third compartment 136, a read chamber 122a, and an additional compartment 132a. The first, second, and third compartments 118a, 120a, and 136 are in (or are capable of being in) fluidic communication with one another as illustrated in the Figure, and the compartments 118a, 120a, and 136 are illustrated as containing the assay compositions 124a, 126a, 128a, and 130a, as described in greater detail herein below. The third compartment 136 is in (or is capable of being in) fluidic communication with the read chamber 122a. The additional compartment 132a is in (or is capable of being in) fluidic communication with one or more of the inlet channel 116a, the compartments 118a, 120a, and 136, and/or the read chamber 122a. The additional compartment 132a contains a predetermined amount of at least one reagent 134a, such as an excipient, diluent, wash solution, etc.

For purposes of example only, the first compartment 118a is illustrated as containing a predetermined amount of each of the first and second compositions 124a and 126a, the second compartment 120a is illustrated as containing a predetermined amount of the third composition 128a, and the third compartment 136 is illustrated as containing a predetermined amount of sensitizer 130a. However, it is to be understood that the four compositions 124a, 126a, 128a, and 130a may be disposed in any order within the microfluidics device 110a, so long as the microfluidics device 110a is capable of functioning in accordance with the presently disclosed and claimed inventive concept(s). In addition, while the third composition 128a and the sensitizer 130a are depicted as being two separate components, it will be understood that the third composition 128a and sensitizer 130a may be associated with one another prior to disposal within the microfluidics device 110a. Further, while the four compositions 124a, 126a, 128a, and 130a are depicted as being separate components, two or more of the separate components may be lyophilized together into a single particle and disposed in any of the compartments 118a, 120a, or 36.

Figure 12:
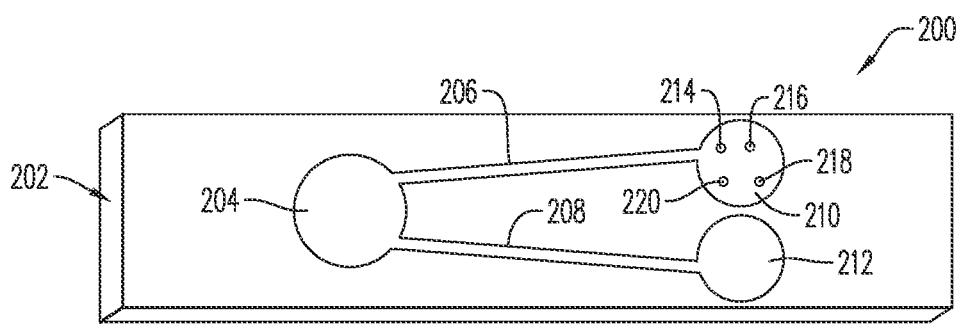
FIG. 12 illustrates a yet further embodiment of a basic architecture for a microfluidics device constructed in accordance with the presently disclosed and claimed inventive concept(s).

As stated herein above, any of the assay structures described herein above may be multiplexed with additional assay(s) in a single microfluidics device. FIG. 12 depicts another embodiment of a microfluidics device constructed in accordance with the presently disclosed and claimed inventive concept(s). The microfluidics device is indicated by the general reference numeral 200 and is similar to the microfluidics devices 10, 10a, 40, 40a, 80, 110, and 110a of FIGS. 5-11, except that the microfluidics device 200 contains multiple compartments that provide a multiplexed assay format. The microfluidics device 200 includes a housing 202 that includes a sample application chamber 204, a first inlet channel 206, a second inlet channel 208, a first compartment 210, and a second compartment 212. A sample (such as, but not limited to, a blood sample) may be applied to the sample application chamber 204, which is in (or is capable of being in) fluidic communication with the inlet channels 206 and 208. The first inlet channel 206 is in (or capable of being in) fluidic communication with the first compartment 210. The first inlet channel 206 and the first compartment 210 represent the assay structure described in detail herein above, and FIG. 12 illustrates the simplest embodiment thereof (i.e., wherein the first compartment 210 contains the first, second, and third compositions 214, 216, and 218, and sensitizer 220). While this depicted assay structure is similar to that depicted in FIG. 7, it is to be understood that any of the other assay structures described herein above or otherwise contemplated herein may be utilized in the multiplexed assay microfluidics device.

The microfluidics device 200 is also provided with a second inlet channel 208 that is in (or capable of being in) fluidic communication with the second compartment 212. The second inlet channel 208 and the second compartment 212 are depicted simply to illustrate the presence of a second assay structure; it is to be understood that any assay structure/architecture may be multiplexed with any of the assays described or otherwise contemplated therein, and thus multiple compartments may be present as necessary to provide the required structure associated with the second assay. In addition, it should also be understood that the second compartment 212 may be provided with reagents similar to those present in the first compartment 210, so that multiple assays detecting different analytes by the same assay mechanism are present in the same microfluidics device. Alternatively, the second compartment 212 may represent a completely different assay format; the only requirement is that this second assay format be capable of being multiplexed with one of the assays described herein.

EXAMPLES

Examples are provided hereinbelow. However, the presently disclosed and claimed inventive concept(s) is to be understood to not be limited in its application to the specific experimentation, results and laboratory procedures. Rather, the Examples are simply provided as one of various embodiments and are meant to be exemplary, not exhaustive.

Example 1

Figure 13:
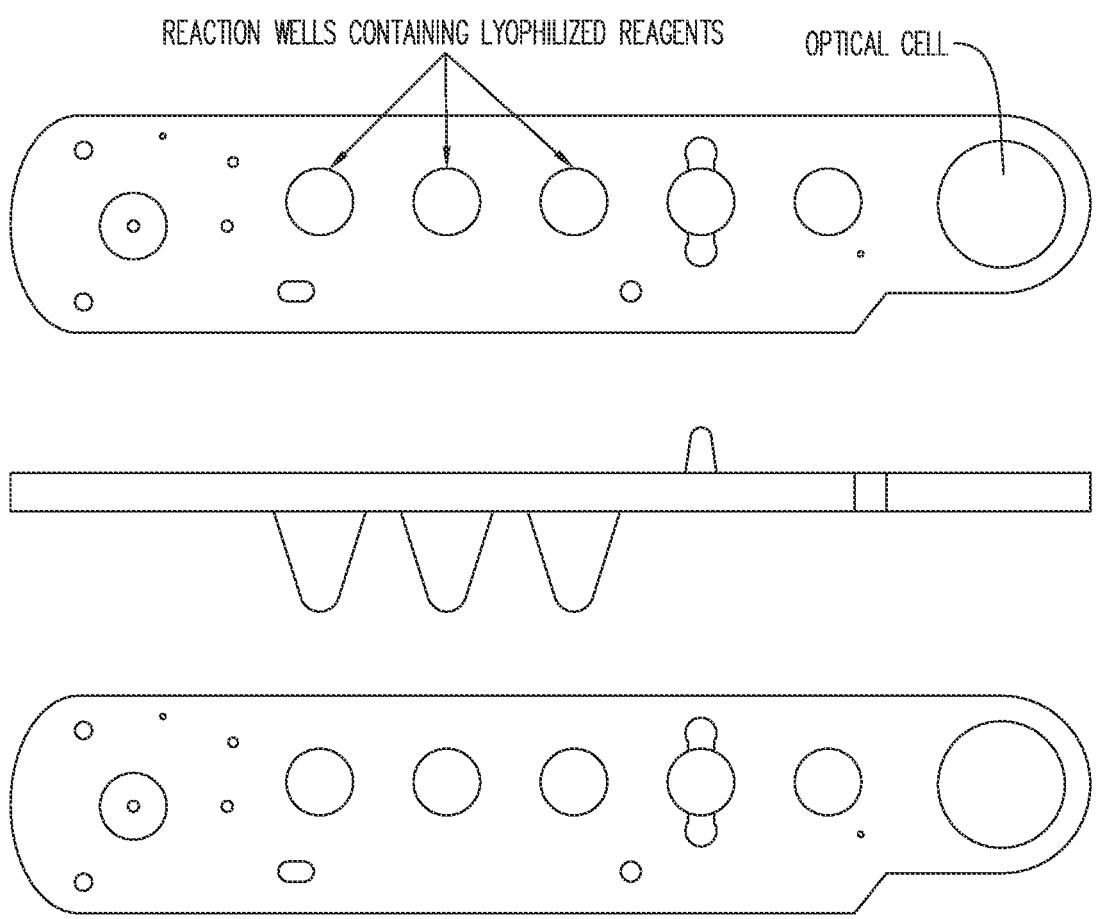
FIG. 13 contains photographic images of a microfluidics device constructed in accordance with the basic device architecture shown in FIG. 6.

FIG. 13 contains photographs of one embodiment of an open system microfluidics device constructed in accordance with the presently disclosed and claimed inventive concept(s). The microfluidics device shown in FIG. 13 contains a similar basic architecture to that of the microfluidics device 10a depicted in FIG. 6. The compartment labeled "optical cell" in FIG. 13 represents the read chamber 28 of the microfluidics device 10a, while the "reaction wells containing lyophilized reagents" represent the first, second, and third compartments 14a, 24, and 26 of the microfluidics device 10a.

The sample is manually added to a first reaction well and incubated with assay component(s) contained therein, and then the resulting reaction/incubation mixture is manually transferred to another well for incubation with assay component(s) contained therein. The final reaction/incubation mixture is then manually transferred to the optical cell for activation of the sensitizer. A diluent may be manually added to the reaction/incubation mixture at any point (or multiple points); that is, a diluent may be added to any of the reaction well(s) and/or to the optical cell.

Example 2

Figure 14:
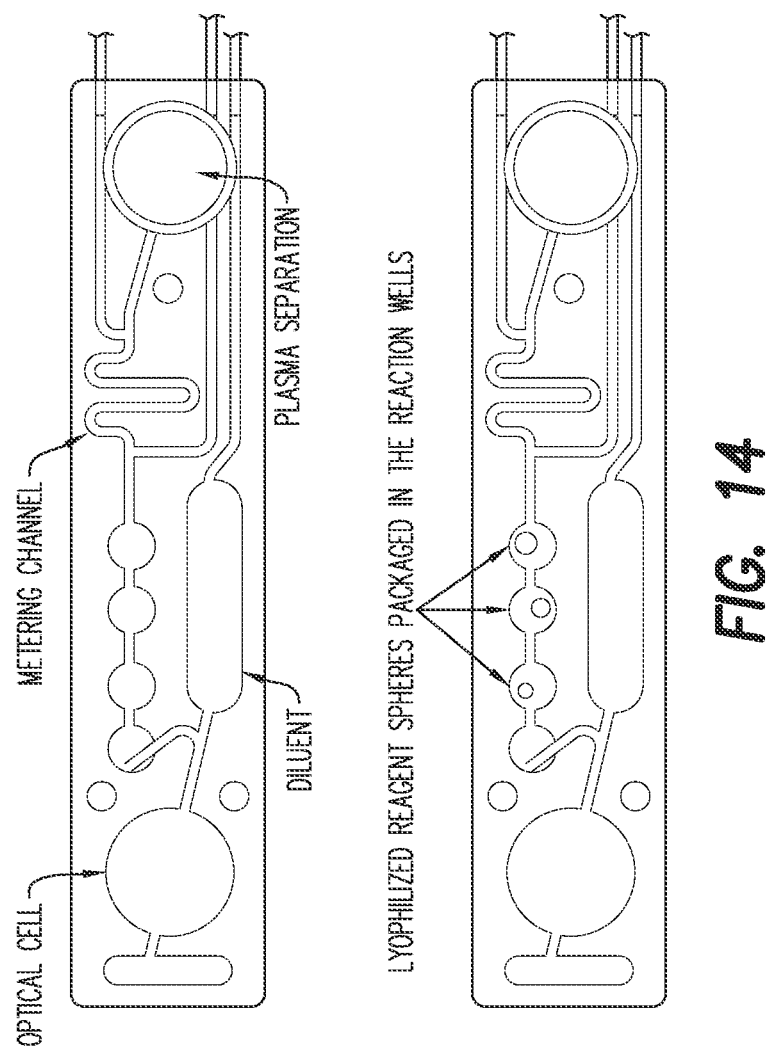
FIG. 14 contains photographic images of a microfluidics device constructed in accordance with the basic device architecture shown in FIG. 11.

FIG. 14 contains photographs of one embodiment of a closed system microfluidics device constructed in accordance with the presently disclosed and claimed inventive concept(s). The microfluidics device shown in FIG. 14 contains a similar basic architecture to that of the microfluidics device 110a depicted in FIG. 11. The compartment labeled "optical cell" in FIG. 14 represents the read chamber 122a of the microfluidics device 110a, while the "lyophilized reagent spheres packaged in the reaction wells" represent the compositions 124a, 126a, 128a, and 130a disposed in the first, second, and third compartments 118a, 120a, and 136 of the microfluidics device 110a. In addition, the compartment labeled "diluent" represents the additional compartment 132a containing the reagent 134a.

In addition, FIG. 14 illustrates the presence of additional structures that are placed upstream of the assay reagents and that allow for separation of certain components of a sample from a whole sample and/or delivery of said components to the assay compartment(s). These components include a plasma separation chamber (which may be included as part of the sample application chamber 114a in FIG. 11) and a metering channel (which may be included as part of the inlet channel 116a in FIG. 11).

Example 3

This Example provides an epitope combination for use in cTnI immunoassays that utilize three antibodies/binding fragments, in accordance with the presently disclosed and claimed inventive concept(s). In certain embodiments, it is desired that the three epitopes be located within the interior (core section) of the cTnI sequence, as the N-terminus and C-terminus of the cTnI molecule is subject to proteolysis both by proteases present in necrotic myocardium and in the patient's plasma.

In the cTnI immunoassay illustrated in FIG. 15, the first and second antibodies/binding fragments bind to overlapping epitopes within region B of FIG. 4 (i.e., SEQ ID NO:3), while the third antibody/binding fragment binds to an epitope within region C of FIG. 4 (i.e., SEQ ID NO:4). In particular, the first antibody/binding fragment specifically binds to the epitope of SEQ ID NO:8, and the second antibody/binding fragment specifically binds to the epitope of SEQ ID NO:9. The epitopes of SEQ ID NOS:8 and 9 are both linear epitopes that are each formed of a continuous amino acid sequence of cTnI. SEQ ID NOS:8 and 9 overlap one another from a linear standpoint, and an antibody/binding fragment that specifically binds to SEQ ID NO:9 cannot bind to cTnI when an antibody/binding fragment that specifically recognizes SEQ ID NO:8 is bound thereto; likewise, and an antibody/binding fragment that specifically binds to SEQ ID NO:8 cannot bind to cTnI when an antibody/binding fragment that specifically recognizes SEQ ID NO:9 is bound thereto. The third antibody or binding fragment thereof specifically binds to the linear epitope of SEQ ID NO:10. SEQ ID NO:10 does not overlap with either of SEQ ID NO:8 or 9, so that an antibody/binding fragment bound to the epitope of either of SEQ ID NO:8 or 9 does not interfere with the binding of another antibody/binding fragment to the epitope of SEQ ID NO:10; thus, the third antibody/binding fragment and one of the first and second antibodies/binding fragments can both bind to a single cTnI molecule.

Example 4

This Example provides another epitope combination for use in cTnI immunoassays that utilize three antibodies/binding fragments, in accordance with the presently disclosed and claimed inventive concept(s). In the cTnI immunoassay illustrated in FIG. 16, the first and second antibodies/binding fragments bind to overlapping epitopes within region B of FIG. 4 (i.e., SEQ ID NO:3), while the third antibody/binding fragment binds to an epitope within region C of FIG. 4 (i.e., SEQ ID NO:4). In particular, the first antibody/binding fragment specifically binds to the epitope of SEQ ID NO:9, and the second antibody/binding fragment specifically binds to the epitope of SEQ ID NO: 11. The epitopes of SEQ ID NOS:9 and 11 are both linear amino acid epitopes that are each formed of a continuous amino acid sequence of cTnI. SEQ ID NOS:9 and 11 overlap one another from a linear standpoint, and an antibody/binding fragment that specifically binds to SEQ ID NO:11 cannot bind to cTnI when an antibody/binding fragment that specifically recognizes SEQ ID NO:9 is bound thereto; likewise, an antibody/binding fragment that specifically binds to SEQ ID NO:9 cannot bind to cTnI when an antibody/binding fragment that specifically recognizes SEQ ID NO:11 is bound thereto. The third antibody or binding fragment thereof specifically binds to the linear epitope of SEQ ID NO:10. SEQ ID NO:10 does not overlap with either of SEQ ID NO:9 or 11, so that an antibody/binding fragment bound to the epitope of either of SEQ ID NO:9 or 11 does not interfere with the binding of another antibody/binding fragment to the epitope of SEQ ID NO:10; thus, the third antibody/binding fragment and one of the first and second antibodies/binding fragments can both bind to a single cTnI molecule.

Example 5

This Example provides yet another epitope combination for use in cTnI immunoassays that utilize three antibodies/binding fragments, in accordance with the presently disclosed and claimed inventive concept(s). In the cTnI immunoassay illustrated in FIG. 17, the first antibody/binding fragment specifically binds to the epitope of SEQ ID NO:12 in epitope region A of FIG. 4 (i.e., SEQ ID NO:2), the second antibody/binding fragment specifically binds to the epitope of SEQ ID NO:13 in epitope region F of FIG. 4 (i.e., SEQ ID NO:7), and the third antibody or binding fragment thereof specifically binds to the epitope of SEQ ID NO:14 in epitope region B of FIG. 4 (i.e., SEQ ID NO:3). While the epitopes of SEQ ID NOS:12 and 13 may not overlap from a linear structural perspective, these two epitopes may overlap in the three-dimensional, conformational structure of the cTnI molecule.

This epitope combination provides an alternative way to obtain higher sensitivity for the cTnI immunoassay. In this case, one capture antibody/binding fragment specifically binds to the epitope of SEQ ID NO:12, which is located in the unstable, processed N-terminal section of the cTnI molecule, while the other capture antibody/binding fragment specifically binds to the epitope of SEQ ID NO:13, which is located in the unstable, processed C-terminal section of the cTnI molecule. The detector antibody/binding fragment, however, binds to the epitope of SEQ ID NO:14, which is located in the stable core section of the molecule.

Example 6

This Example provides an epitope combination for use in BNP immunoassays that utilize three antibodies/binding fragments, in accordance with the presently disclosed and claimed inventive concept(s). FIG. 18 depicts the 32 amino acid sequence of BNP (assigned SEQ ID NO:15) and the three epitopes of this non-limiting example.

In particular, the first antibody/binding fragment specifically binds to the epitope of SEQ ID NO:16, and the second antibody/binding fragment specifically binds to the epitope of SEQ ID NO:17. The epitopes of SEQ ID NOS:16 and 17 are both linear epitopes that are each formed of a continuous amino acid sequence of BNP. SEQ ID NOS:16 and 17 overlap one another, and an antibody/binding fragment that specifically binds to SEQ ID NO:17 cannot bind to BNP when an antibody/binding fragment that specifically recognizes SEQ ID NO:16 is bound thereto; likewise, an antibody/binding fragment that specifically binds to SEQ ID NO:16 cannot bind to BNP when an antibody/binding fragment that specifically recognizes SEQ ID NO:17 is bound thereto. The third antibody or binding fragment thereof specifically binds to the linear epitope of SEQ ID NO:18. SEQ ID NO:18 does not overlap with either of SEQ ID NO:16 or 17, so that an antibody/binding fragment bound to the epitope of either of SEQ ID NO:16 or 17 does not interfere with the binding of another antibody/binding fragment to the epitope of SEQ ID NO:18. Thus, the third antibody/binding fragment and one of the first and second antibodies/binding fragments can both bind to a single BNP molecule.

Therefore, in accordance with the presently disclosed and claimed inventive concept(s), there has been provided compositions comprising a chemiluminescent system, as well as kits and microfluidics devices containing same and methods of use thereof, that fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

Illustrative Embodiments

Illustrative embodiments are provided herein below. However, the presently disclosed and claimed inventive concept(s) is to be understood to not be limited in its application to the specific experimentation, results and laboratory procedures. Rather, the Illustrative embodiments are simply provided as one of various embodiments and are meant to be exemplary, not exhaustive.

Illustrative embodiment 1: a kit containing a chemiluminescent detection system for a specific analyte, the kit comprising:
    a first composition comprising a singlet-oxygen activatable chemiluminescent compound and a first antibody or binding fragment thereof associated therewith, wherein the first antibody or binding fragment thereof is a detection antibody that specifically binds to a first epitope of the analyte whereby the singlet-oxygen activatable chemiluminescent compound is capable of indirectly binding to the analyte via the first antibody or binding fragment thereof;
    (b) a second composition comprising a singlet-oxygen activatable chemiluminescent compound and a second antibody or binding fragment thereof associated therewith, wherein the second antibody or binding fragment thereof is a detection antibody that specifically binds to a second epitope of the analyte whereby the singlet-oxygen activatable chemiluminescent compound is capable of indirectly binding to the analyte via the second antibody or binding fragment thereof, and wherein the first and second epitopes at least partially overlap such that the first and second antibodies or binding fragments thereof cannot both bind to a single analyte molecule; and (c) a third composition comprising a third antibody or binding fragment thereof, the third antibody or binding fragment thereof being a capture antibody that specifically binds to a third epitope of the analyte that does not overlap with the first and second epitopes, whereby a single analyte molecule can bind the third antibody or binding fragment thereof and one of the first and second antibodies or binding fragments thereof, and wherein the third antibody or binding fragment thereof is capable of association with a sensitizer capable of generating singlet oxygen in its excited state, whereby association of the third antibody or binding fragment thereof with the sensitizer allows for the indirect binding of the sensitizer to the analyte.

Illustrative embodiment 2: the kit of Illustrative embodiment 1, further comprising the sensitizer.

Illustrative embodiment 3: the kit of Illustrative embodiment 2, wherein the third composition further comprises the sensitizer associated with the third antibody or binding fragment thereof.

Illustrative embodiment 4: The kit of illustrative embodiment 2 or 3, wherein the third antibody or binding fragment thereof is biotinylated, and wherein the sensitizer has streptavidin associated therewith.

Illustrative embodiment 5: The kit of illustrative embodiment 4, further comprising a microfluidics device in which (a)-(c) are disposed.

Illustrative embodiment 6: The kit of any of illustrative embodiments 1-5, further comprising a diluent.

Illustrative embodiment 7: The kit of any of illustrative embodiments 1-6, wherein the singlet-oxygen activatable chemiluminescent compounds of the first and second compositions are the same.

Illustrative embodiment 8: The kit of any of illustrative embodiments 1-6, wherein the singlet-oxygen activatable chemiluminescent compounds of the first and second compositions are different.

Illustrative embodiment 9: The kit of any of illustrative embodiments 1-8, wherein at least one of the first and second compositions further comprises at least one fluorescent molecule that is excited by the activated chemiluminescent compound.

Illustrative embodiment 10: The kit of any of illustrative embodiments 1-9, wherein at least one of (a)-(c) is further defined as being in the form of a lyophilized reagent.

Illustrative embodiment 11: The kit of illustrative embodiment 10, wherein (a) and (b) are lyophilized together.

Illustrative embodiment 12. The kit of illustrative embodiment 10 or 11, further comprising an excipient for the reconstitution of the lyophilized reagent.

Illustrative embodiment 13: The kit of any of illustrative embodiments 1-12, wherein at least one of the first, second, and third antibodies or binding fragments thereof is a polyclonal antibody.

Illustrative embodiment 14: The kit of any of illustrative embodiments 1-13, wherein at least one of the first, second, and third antibodies or binding fragments thereof is a monoclonal antibody.

Illustrative embodiment 15: The kit of any of illustrative embodiments 1-14, wherein the analyte is Troponin I.

Illustrative embodiment 16: The kit of illustrative embodiment 15, wherein at least one of:

(a) the first and second antibodies or binding fragments thereof specifically bind to overlapping epitopes within SEQ ID NO:2, and the third antibody or binding fragment thereof specifically binds to an epitope within one of SEQ ID NOS:3-7; (b) the first and second antibodies or binding fragments thereof specifically bind to overlapping epitopes within SEQ ID NO:3, and the third antibody or binding fragment thereof specifically binds to an epitope within one of SEQ ID NOS:2 and 4-7;

(c) the first and second antibodies or binding fragments thereof specifically bind to overlapping epitopes within SEQ ID NO:4, and the third antibody or binding fragment thereof specifically binds to an epitope within one of SEQ ID NOS:2-3 and 5-7;

(d) the first and second antibodies or binding fragments thereof specifically bind to overlapping epitopes within SEQ ID NO:5, and the third antibody or binding fragment thereof specifically binds to an epitope within one of SEQ ID NOS:2-4 and 6-7;

(e) the first and second antibodies or binding fragments thereof specifically bind to overlapping epitopes within SEQ ID NO:6, and the third antibody or binding fragment thereof specifically binds to an epitope within one of SEQ ID NOS:2-5 and 7; and (f) the first and second antibodies or binding fragments thereof specifically bind to overlapping epitopes within SEQ ID NO:7, and the third antibody or binding fragment thereof specifically binds to an epitope within one of SEQ ID NOS:2-6.

Illustrative embodiment 17: The kit of illustrative embodiment 15 or 16, wherein at least one of:

(i) the first antibody or binding fragment thereof specifically binds to an epitope of one of SEQ ID NOS:8, 9, and 11, the second antibody or binding fragment thereof specifically binds to an epitope of one of SEQ ID NOS:8, 9, and 11, and the third antibody or binding fragment thereof specifically binds to an epitope of SEQ ID NO:10; and (ii) the first antibody or binding fragment thereof specifically binds to an epitope of SEQ ID NO:12 or 13, the second antibody or binding fragment thereof specifically binds to an epitope of SEQ ID NO:12 or 13, and the third antibody or binding fragment thereof specifically binds to an epitope of SEQ ID NO:14.

Illustrative embodiment 18: A microfluidics device, comprising: at least one compartment containing:

(i) a first composition comprising a singlet-oxygen activatable chemiluminescent compound and a first antibody or binding fragment thereof associated therewith, wherein the first antibody or binding fragment thereof is a detection antibody that specifically binds to a first epitope of a specific analyte whereby the singlet-oxygen activatable chemiluminescent compound is capable of indirectly binding to the analyte via the first antibody or binding fragment thereof;

(ii) a second composition comprising a singlet-oxygen activatable chemiluminescent compound and a second antibody or binding fragment thereof associated therewith, wherein the second antibody or binding fragment thereof is a detection antibody that specifically binds to a second epitope of the analyte whereby the singlet-oxygen activatable chemiluminescent compound is capable of indirectly binding to the analyte via the second antibody or binding fragment thereof, and wherein the first and second epitopes at least partially overlap such that the first and second antibodies or binding fragments thereof cannot both bind to a single analyte molecule; and (iii) a third composition comprising a third antibody or binding fragment thereof, the third antibody or binding fragment thereof being a capture antibody that specifically binds to a third epitope of the analyte that does not overlap with the first and second epitopes, whereby a single analyte molecule can bind the third antibody or binding fragment thereof and one of the first and second antibodies or binding fragments thereof; and (iv) a sensitizer capable of association with the third antibody or binding fragment thereof, the sensitizer being capable of generating singlet oxygen in its excited state, and wherein association of the third antibody or binding fragment thereof with the sensitizer allows for the indirect binding of the sensitizer to the analyte.

Illustrative embodiment 19: The microfluidics device of illustrative embodiment 18, wherein (i)-(iv) are disposed in the same compartment.

Illustrative embodiment 20: The microfluidics device of illustrative embodiment 19, wherein the sensitizer is associated with the third antibody or binding fragment thereof.

Illustrative embodiment 21: The microfluidics device of any of illustrative embodiments 18-20, further comprising an inlet channel through which a sample may be disposed, wherein the at least one compartment is capable of being in fluidic communication with the inlet channel.

Illustrative embodiment 22: The microfluidics device of illustrative embodiment 18, further defined as comprising at least two compartments, wherein a first compartment contains (i), (ii), and (iii), and wherein a second compartment contains (iv).

Illustrative embodiment 23: The microfluidics device of illustrative embodiment 22, further comprising an inlet channel through which a sample may be disposed, wherein the first compartment is capable of being in fluidic communication with the inlet channel, and wherein the second compartment is capable of being in fluid communication with at least one of the inlet channel and the first compartment.

Illustrative embodiment 24: The microfluidics device of any of illustrative embodiments 18-23, wherein the third antibody or binding fragment thereof is biotinylated, and wherein the sensitizer has streptavidin associated therewith.

Illustrative embodiment 25: The microfluidics device of any of illustrative embodiments 18-24, wherein the singlet-oxygen activatable chemiluminescent compounds of the first and second compositions are the same.

Illustrative embodiment 26: The microfluidics device of any of illustrative embodiments 18-24, wherein the singlet-oxygen activatable chemiluminescent compounds of the first and second compositions are different.

Illustrative embodiment 27: The microfluidics device of any of illustrative embodiments 18-25, wherein at least one of the first and second compositions further comprises at least one fluorescent molecule that is excited by the activated chemiluminescent compound.

Illustrative embodiment 28: The microfluidics device of any of illustrative embodiments 18-27, wherein at least one of (i), (ii), (iii), and (iv) is further defined as being in the form of a lyophilized reagent.

Illustrative embodiment 29: The microfluidics device of illustrative embodiment 28, wherein (a) and (b) are lyophilized together.

Illustrative embodiment 30. The microfluidics device of illustrative embodiment 28 or 29, further comprising at least one additional compartment capable of being in fluidic communication with the inlet channel and the at least one compartment, wherein the at least one additional compartment contains an excipient for reconstitution of the at least one lyophilized reagent.

Illustrative embodiment 31: The microfluidics device of any of illustrative embodiments 18-30, further comprising at least one additional compartment capable of being in fluidic communication with at least one of the inlet channel and the at least one compartment, and wherein the at least one additional compartment contains a diluent.

Illustrative embodiment 32: The microfluidics device of any of illustrative embodiments 18-30, further comprising at least one additional compartment that allows for separation of components of the sample prior to incubation with any of (i)-(iv).

Illustrative embodiment 33: The microfluidics device of any of illustrative embodiments 18-32, wherein at least one of the first, second, and third antibodies or binding fragments thereof is a polyclonal antibody.

Illustrative embodiment 34: The microfluidics device of any of illustrative embodiments 18-33, wherein at least one of the first, second, and third antibodies or binding fragments thereof is a monoclonal antibody.

Illustrative embodiment. The microfluidics device of any of illustrative embodiments 18-34, wherein the analyte is Troponin I.

Illustrative embodiment 36: The microfluidics device of illustrative embodiment 35, wherein at least one of:

(a) the first and second antibodies or binding fragments thereof specifically bind to overlapping epitopes within SEQ ID NO:2, and the third antibody or binding fragment thereof specifically binds to an epitope within one of SEQ ID NOS:3-7; (b) the first and second antibodies or binding fragments thereof specifically bind to overlapping epitopes within SEQ ID NO:3, and the third antibody or binding fragment thereof specifically binds to an epitope within one of SEQ ID NOS:2 and 4-7;

(c) the first and second antibodies or binding fragments thereof specifically bind to overlapping epitopes within SEQ ID NO:4, and the third antibody or binding fragment thereof specifically binds to an epitope within one of SEQ ID NOS:2-3 and 5-7;

(d) the first and second antibodies or binding fragments thereof specifically bind to overlapping epitopes within SEQ ID NO:5, and the third antibody or binding fragment thereof specifically binds to an epitope within one of SEQ ID NOS:2-4 and 6-7;

(e) the first and second antibodies or binding fragments thereof specifically bind to overlapping epitopes within SEQ ID NO:6, and the third antibody or binding fragment thereof specifically binds to an epitope within one of SEQ ID NOS:2-5 and 7; and (f) the first and second antibodies or binding fragments thereof specifically bind to overlapping epitopes within SEQ ID NO:7, and the third antibody or binding fragment thereof specifically binds to an epitope within one of SEQ ID NOS:2-6.

Illustrative embodiment 37: The microfluidics device of illustrative embodiment 35 or 36, wherein:

(i) the first antibody or binding fragment thereof specifically binds to an epitope of one of SEQ ID NOS:8, 9, and 11, the second antibody or binding fragment thereof specifically binds to an epitope of one of SEQ ID NOS:8, 9, and 11, and the third antibody or binding fragment thereof specifically binds to an epitope of SEQ ID NO:10; and (ii) the first antibody or binding fragment thereof specifically binds to an epitope of SEQ ID NO:12 or 13, the second antibody or binding fragment thereof specifically binds to an epitope of SEQ ID NO:12 or 13, and the third antibody or binding fragment thereof specifically binds to an epitope of SEQ ID NO:14.

Illustrative embodiment 38: A method for detecting the presence and/or concentration of a specific analyte in a sample, comprising the steps of:

(a) combining, either simultaneously or wholly or partially sequentially:
  (i) a sample suspected of containing the specific analyte;
  (ii) a first composition comprising a singlet-oxygen activatable chemiluminescent compound and a first antibody or binding fragment thereof associated therewith, wherein the first antibody or binding fragment thereof is a detection antibody that specifically binds to a first epitope of a specific analyte;
  (iii) a second composition comprising a singlet-oxygen activatable chemiluminescent compound and a second antibody or binding fragment thereof associated therewith, wherein the second antibody or binding fragment thereof is a detection antibody that specifically binds to a second epitope of the analyte, and wherein the first and second epitopes at least partially overlap such that the first and second antibodies or binding fragments thereof cannot both bind to a single analyte molecule;
  (iv) a third composition comprising a third antibody or binding fragment thereof, the third antibody or binding fragment thereof being a capture antibody that specifically binds to a third epitope of the analyte that does not overlap with the first and second epitopes, whereby a single analyte molecule can bind the third antibody or binding fragment thereof and one of the first and second antibodies or binding fragments thereof; and
  (v) a sensitizer capable of association with the third antibody or binding fragment thereof, the sensitizer being capable of generating singlet oxygen in its excited state;
(b) allowing the binding of (ii), (iii) and/or (iv) to analyte within the sample, wherein a first sandwich complex comprising an analyte molecule and (ii) and (iv) is formed, and a second sandwich complex comprising another analyte molecule and (iii) and (iv) is formed, and wherein (v) associates with (iv) in the first and second sandwich complexes, thus bringing the sensitizer into close proximity to the chemiluminescent compounds of (ii) and (iii);
(c) activating the sensitizer to generate singlet oxygen, wherein activation of the sensitizer present in the first and second sandwich complexes causes the activation of the chemiluminescent compounds present in the first and second sandwich complexes;
(d) determining the amount of chemiluminescence generated by the activated chemiluminescent compounds present in the first and second sandwich complexes;
(e) optionally repeating steps (b)-(d); and
(f) detecting the presence and/or concentration of the analyte by analyzing the amount of chemiluminescence so produced, wherein the amount of chemiluminescence is directly proportional to the amount of analyte in the sample.

Illustrative embodiment 39: The method of illustrative embodiment 38, wherein the sensitizer is a photosensitizer, and wherein step (c) is further defined as activating the photosensitizer via irradiation with light.

Illustrative embodiment 40: The method of illustrative embodiment 38 or 39, wherein the sample is selected from the group consisting of whole blood, plasma, serum, saliva, sputum, cerebrospinal fluid (CSF), skin, interstitial fluid, tears, mucus, urine, swabs, and combinations thereof.

Illustrative embodiment 41: The method of illustrative embodiment 40, further comprising a step of exposing the sample to a separation step prior to combining with any of (ii)-(v).

Illustrative embodiment 42: The method of any of illustrative embodiments 38-41, wherein the third antibody or binding fragment thereof is biotinylated, and wherein the sensitizer has streptavidin associated therewith.

Illustrative embodiment 43: The method of any of illustrative embodiments 38-42, wherein the singlet-oxygen activatable chemiluminescent compounds of the first and second compositions are the same.

Illustrative embodiment 44: The method of any of illustrative embodiments 38-43, wherein the singlet-oxygen activatable chemiluminescent compounds of the first and second compositions are different.

Illustrative embodiment 45: The method of any of illustrative embodiments 38-44, wherein at least one of the first and second compositions further comprises at least one fluorescent molecule that is excited by the activated chemiluminescent compound.

Illustrative embodiment 46: The method of illustrative embodiment 45, further comprising a step of measuring the amount of light emitted by the fluorescent molecules to determine the amount of analyte in the sample.

Illustrative embodiment 47: The method of any of illustrative embodiments 38-46, further comprising a step of diluting the mixture of (i)-(v) prior to step (c).

Illustrative embodiment 48: The method of any of illustrative embodiments 38-47, wherein at least one of the first, second, and third antibodies or binding fragments thereof is a polyclonal antibody.

Illustrative embodiment 49: The method of any of illustrative embodiments 38-48, wherein at least one of the first, second, and third antibodies or binding fragments thereof is a monoclonal antibody.

Illustrative embodiment 50: The method of any of illustrative embodiments 38-49, wherein the analyte is Troponin I.

Illustrative embodiment 51: The method of illustrative embodiment 50, wherein:
  (a) the first and second antibodies or binding fragments thereof specifically bind to overlapping epitopes within SEQ ID NO:2, and the third antibody or binding fragment thereof specifically binds to an epitope within one of SEQ ID NOS:3-7;
  (b) the first and second antibodies or binding fragments thereof specifically bind to overlapping epitopes within SEQ ID NO:3, and the third antibody or binding fragment thereof specifically binds to an epitope within one of SEQ ID NOS:2 and 4-7;
  (c) the first and second antibodies or binding fragments thereof specifically bind to overlapping epitopes within SEQ ID NO:4, and the third antibody or binding fragment thereof specifically binds to an epitope within one of SEQ ID NOS:2-3 and 5-7;

(d) the first and second antibodies or binding fragments thereof specifically bind to overlapping epitopes within SEQ ID NO:5, and the third antibody or binding fragment thereof specifically binds to an epitope within one of SEQ ID NOS:2-4 and 6-7;

(e) the first and second antibodies or binding fragments thereof specifically bind to overlapping epitopes within SEQ ID NO:6, and the third antibody or binding fragment thereof specifically binds to an epitope within one of SEQ ID NOS:2-5 and 7; and (f) the first and second antibodies or binding fragments thereof specifically bind to overlapping epitopes within SEQ ID NO:7, and the third antibody or binding fragment thereof specifically binds to an epitope within one of SEQ ID NOS:2-6.

Illustrative embodiment 52: The method of illustrative embodiments 50 or 51, wherein:

(i) the first antibody or binding fragment thereof specifically binds to an epitope of one of SEQ ID NOS:8, 9, and 11, the second antibody or binding fragment thereof specifically binds to an epitope of one of SEQ ID NOS:8, 9, and 11, and the third antibody or binding fragment thereof specifically binds to an epitope of SEQ ID NO:10; and (ii) the first antibody or binding fragment thereof specifically binds to an epitope of SEQ ID NO:12 or 13, the second antibody or binding fragment thereof specifically binds to an epitope of SEQ ID NO:12 or 13, and the third antibody or binding fragment thereof specifically binds to an epitope of SEQ ID NO:14.

What is claimed is:

1. A method for detecting the presence and/or concentration of a specific analyte in a sample, comprising the steps of:
   (a) combining, either simultaneously or wholly or partially sequentially, components (i), (ii), (iii), (iv), and (v) within a compartment to form a reaction mixture:
      (i) a sample suspected of containing the specific analyte;
      (ii) a first composition comprising a singlet-oxygen activatable chemiluminescent compound and a first antibody or binding fragment thereof associated therewith, wherein the first antibody or binding fragment thereof is a detection antibody that specifically binds to a first epitope of a specific analyte;
      (iii) a second composition comprising a singlet-oxygen activatable chemiluminescent compound and a second antibody or binding fragment thereof associated therewith, wherein the second antibody or binding fragment thereof is a detection antibody that specifically binds to a second epitope of the analyte, and wherein the first and second epitopes at least partially overlap such that the first and second antibodies or binding fragments thereof cannot both bind to a single analyte molecule, and wherein the first and second epitopes are not identical, and wherein the first antibody or binding fragment thereof has a higher affinity for the analyte than the second antibody or binding fragment thereof while the second antibody or fragment thereof has a greater dynamic assay range than the first antibody or fragment thereof, and wherein the singlet-oxygen activatable chemiluminescent compounds of the first and second compositions are different;
      (iv) a third composition comprising a third antibody or binding fragment thereof, the third antibody or binding fragment thereof being a capture antibody that specifically binds to a third epitope of the analyte that does not overlap with the first and second epitopes, whereby a single analyte molecule can bind the third antibody or binding fragment thereof and one of the first and second antibodies or binding fragments thereof; and
      (v) a sensitizer capable of association with the third antibody or binding fragment thereof, the sensitizer being capable of generating singlet oxygen in its excited state;
   (b) allowing the binding of (ii), (iii) and/or (iv) to analyte within the sample, wherein a first sandwich complex comprising an analyte molecule and (ii) and (iv) is formed, and a second sandwich complex comprising another analyte molecule and (iii) and (iv) is formed, and wherein (v) associates with (iv) in the first and second sandwich complexes, thus bringing the sensitizer into close proximity to the chemiluminescent compounds of (ii) and (iii) in the reaction mixture;
   (c) activating the sensitizer to generate singlet oxygen, wherein activation of the sensitizer present in the first and second sandwich complexes causes the activation of the chemiluminescent compounds present in the first and second sandwich complexes of the reaction mixture;
   (d) determining the amount of chemiluminescence generated by the activated chemiluminescent compounds present in the first and second sandwich complexes of the reaction mixture;
   (e) optionally repeating steps (b)-(d); and
   (f) detecting the presence and/or concentration of the analyte in the sample by analyzing the amount of chemiluminescence generated by the activated chemiluminescent compounds present in the first and second sandwich complexes in the reaction mixture, wherein the amount of chemiluminescence is directly proportional to the amount of analyte in the sample.

2. The method of claim 1, wherein the sensitizer is a photosensitizer, and wherein step (c) is further defined as activating the photosensitizer via irradiation with light.

3. The method of claim 2, further comprising a step of exposing the sample to a separation step prior to combining with any of (ii)-(v).

4. The method of claim 1, wherein at least one of the first and second compositions further comprises at least one fluorescent molecule that is excited by the activated chemiluminescent compound.

5. The method of claim 4, further comprising a step of measuring the amount of light emitted by the fluorescent molecules to determine the amount of analyte in the sample.

6. The method of claim 1, wherein at least one of (ii)-(v) is further defined as being initially provided in the form of a lyophilized reagent, and wherein the method further comprises the step of reconstituting the at least one of (ii)-(v) in an excipient prior to performing step (a).

7. The method of claim 1, wherein the sample is selected from the group consisting of whole blood, plasma, serum, saliva, sputum, cerebrospinal fluid (CSF), skin, interstitial fluid, tears, mucus, urine, swabs, and combinations thereof.

8. The method of claim 1, wherein the third antibody or binding fragment thereof is biotinylated, and wherein the sensitizer has streptavidin associated therewith.

9. The method of claim 1, further comprising a step of diluting the mixture of (i)-(v) prior to step (c).

10. The method of claim 1, wherein at least one of the first, second, and third antibodies or binding fragments thereof is a polyclonal antibody.

11. The method of claim 1, wherein at least one of the first, second, and third antibodies or binding fragments thereof is a monoclonal antibody.

12. The method of claim 1, wherein the analyte is Troponin i.

13. The method of claim 12, wherein the method detects Troponin I concentrations in a range of from about 0.006 ng/ml to about 60 ng/ml.

14. The method of claim 1, wherein the first antibody or binding fragment thereof specifically binds to the analyte with a dissociation constant in a range of from about $10^{-10}$ M to about $10^{-13}$ M, and the second antibody or binding fragment thereof specifically binds to the analyte with a dissociation constant in a range of from about $10^{-6}$ M to about $10^{-10}$ M.

15. The method of claim 1, wherein a combination of the first and second compositions added in step (a) comprises the first composition in a range of from about 5% to about 20% and the second composition in a range of from about 80% to about 95%.

16. The method of claim 1, wherein the first composition is combined with the sample prior to the second composition.

17. The method of claim 1, wherein steps (a)-(f) are performed in the same compartment of a microfluidics device.

18. A method for detecting the presence and/or concentration of Troponin I in a sample, comprising the steps of:
(a) combining, either simultaneously or wholly or partially sequentially, components (i), (ii), (iii), (iv), and (v) within a compartment to form a reaction mixture:
(i) a sample suspected of containing Troponin I;
(ii) a first composition comprising a singlet-oxygen activatable chemiluminescent compound and a first monoclonal antibody or binding fragment thereof associated therewith, wherein the first monoclonal antibody or binding fragment thereof is a detection antibody that specifically binds to a first epitope of Troponin I with a dissociation constant in a range of from about $10^{-10}$ M to about $10^{-13}$ M;
(iii) a second composition comprising a singlet-oxygen activatable chemiluminescent compound and a second monoclonal antibody or binding fragment thereof associated therewith, wherein the second monoclonal antibody or binding fragment thereof is a detection antibody that specifically binds to a second epitope of Troponin I with a dissociation constant in a range of from about $10^{-6}$ M to about $10^{-10}$ M, and wherein the first and second epitopes at least partially overlap such that the first and second monoclonal antibodies or binding fragments thereof cannot both bind to a single Troponin I molecule, and wherein the first and second epitopes are not identical, wherein the second monoclonal antibody or binding fragment thereof has a greater dynamic assay range than the first monoclonal antibody or binding fragment, and wherein the singlet-oxygen activatable chemiluminescent compounds of the first and second compositions are different;
(iv) a third composition comprising a third monoclonal antibody or binding fragment thereof, the third monoclonal antibody or binding fragment thereof being a capture antibody that specifically binds to a third epitope of Troponin I that does not overlap with the first and second epitopes, whereby a single analyte molecule can bind the third monoclonal antibody or binding fragment thereof and one of the first and second monoclonal antibodies or binding fragments thereof; and
(v) a photosensitizer capable of association with the third monoclonal antibody or binding fragment thereof, the photosensitizer being capable of generating singlet oxygen in its excited state;
(b) allowing the binding of (ii), (iii) and/or (iv) to Troponin I within the sample, wherein a first sandwich complex comprising a Troponin I molecule and (ii) and (iv) is formed, and a second sandwich complex comprising another Troponin I molecule and (iii) and (iv) is formed, and wherein (v) associates with (iv) in the first and second sandwich complexes, thus bringing the photosensitizer into close proximity to the chemiluminescent compounds of (ii) and (iii) in the reaction mixture;
(c) activating the photosensitizer via irradiation with light to generate singlet oxygen, wherein activation of the photosensitizer present in the first and second sandwich complexes causes the activation of the chemiluminescent compounds present in the first and second sandwich complexes of the reaction mixture;
(d) determining the amount of chemiluminescence generated by the activated chemiluminescent compounds present in the first and second sandwich complexes of the reaction mixture;
(e) optionally repeating steps (b)-(d); and
(f) detecting the presence and/or concentration of Troponin I in the sample by analyzing the amount of chemiluminescence produced by the first sandwich complex in the reaction mixture and the amount of chemiluminescence produced by the second sandwich complex in the reaction mixture, wherein the amount of combined chemiluminescence is directly proportional to the amount of Troponin I in the sample.

19. The method of claim 18, wherein the method detects Troponin I concentrations in a range of from about 0.006 ng/ml to about 60 ng/ml.

20. The method of claim 18, wherein a combination of the first and second compositions added in step (a) comprises the first composition in a range of from about 5% to about 20% and the second composition in a range of from about 80% to about 95%.

\* \* \* \* \*